US012714979B2

(12) United States Patent
Deck et al.

(10) Patent No.: US 12,714,979 B2
(45) Date of Patent: Aug. 25, 2026

(54) ELECTROMECHANICALLY DRIVEN OSCILLATORY FLOW IN FLUIDIC SYSTEMS

(71) Applicant: Massachusetts Institute of Technology, Cambridge, MA (US)

(72) Inventors: Leif-Thore Deck, Eggenstein-Leopoldshafen (DE); Natalie Eyke, Cambridge, MA (US); Travis Hart, Watertown, MA (US); Klavs F. Jensen, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 907 days.

(21) Appl. No.: 17/921,956

(22) PCT Filed: Apr. 28, 2021

(86) PCT No.: PCT/US2021/029522
§ 371 (c)(1),
(2) Date: Oct. 27, 2022

(87) PCT Pub. No.: WO2021/222334
PCT Pub. Date: Nov. 4, 2021

(65) Prior Publication Data

US 2023/0166233 A1 Jun. 1, 2023

Related U.S. Application Data

(60) Provisional application No. 63/016,358, filed on Apr. 28, 2020.

(51) Int. Cl.
*B01J 19/24* (2006.01)
*B01J 19/00* (2006.01)
(Continued)

(52) U.S. Cl.
CPC ......... *B01J 19/241* (2013.01); *B01J 19/0066* (2013.01); *B01J 19/0093* (2013.01);
(Continued)

(58) Field of Classification Search
CPC ...... B01J 19/185; B01J 19/241; B01J 19/285; B01J 19/2465; B01J 19/2415;
(Continued)

(56) References Cited

U.S. PATENT DOCUMENTS 1,783,611 A * 12/1930 Gohring .................... F04B 5/02 417/418
2,927,006 A 3/1960 Brooks
(Continued)

FOREIGN PATENT DOCUMENTS

WO WO 2007/021818 A2 2/2007

OTHER PUBLICATIONS

Abolhasani et al., Oscillatory three-phase flow reactor for studies of bi-phasic catalytic reactions. ChemComm. Apr. 16, 2015; 51(43):8916-9.

(Continued)

*Primary Examiner* — Lessanework Seifu
(74) *Attorney, Agent, or Firm* — Wolf, Greenfield & Sacks, P.C.

(57) ABSTRACT

Fluidic systems and methods in which oscillatory flow is employed are generally described. In some instances, one or more solenoids are used to drive the oscillation of a magnetically-susceptible body which creates oscillatory flow of a fluid in a fluidic channel in fluid communication with a channel containing the magnetically-susceptible body.

20 Claims, 13 Drawing Sheets

(51) Int. Cl.
*B01J 19/18* (2006.01)
*B01L 3/00* (2006.01)
*C07C 45/43* (2006.01)

(52) U.S. Cl.
CPC ......... *B01J 19/185* (2013.01); *B01J 19/2465* (2013.01); *B01L 3/502784* (2013.01); *C07C 45/43* (2013.01); *B01J 2219/00813* (2013.01); *B01J 2219/00889* (2013.01); *B01J 2219/00894* (2013.01); *B01L 2300/088* (2013.01); *B01L 2400/043* (2013.01); *B01L 2400/0666* (2013.01)

(58) Field of Classification Search
CPC ......................... B01J 19/1868; B01J 19/2435; B01J 19/2405; B01J 19/0093; B01J 2219/00813; B01J 2219/00894; B01J 2219/00889; B01J 2219/00858
See application file for complete search history.

(56) References Cited

U.S. PATENT DOCUMENTS

| | | | | |
|---|---|---|---|---|
| 3,791,770 | A | 2/1974 | Farkos | |
| 4,271,007 | A | 6/1981 | Souhrada et al. | |
| 4,489,750 | A | 12/1984 | Nehring | |
| 4,832,500 | A | 5/1989 | Brunold et al. | |
| 5,713,728 | A | 2/1998 | Salamey | |
| 5,899,672 | A | 5/1999 | Salamey | |
| 6,186,412 | B1 | 2/2001 | Bachar | |
| 6,429,268 | B1 | 8/2002 | Xiongwei | |
| 7,665,510 | B2 * | 2/2010 | Nara | F28F 13/10 165/104.28 |
| 9,132,396 | B2 | 9/2015 | Churski et al. | |
| 10,118,149 | B2 | 11/2018 | Reintjens et al. | |
| 10,252,239 | B2 | 4/2019 | Abolhasani et al. | |
| 2006/0120878 | A1 * | 6/2006 | Ghoshal | F04F 1/06 417/48 |
| 2008/0226477 | A1 | 9/2008 | Wu et al. | |
| 2009/0034359 | A1 | 2/2009 | Cardonne et al. | |
| 2009/0304890 | A1 | 12/2009 | Ni et al. | |
| 2012/0171090 | A1 | 7/2012 | Chang | |
| 2014/0147908 | A1 | 5/2014 | Jakiela et al. | |
| 2016/0318015 | A1 * | 11/2016 | Kornilovich | B41J 2/14201 |

OTHER PUBLICATIONS

Asghari et al., Oscillatory Viscoelastic Microfluidics for Efficient Focusing and Separation of Nanoscale Species. ACS Nano. Jan. 28, 2020;14(1):422-433. doi: 10.1021/acsnano.9b06123. Epub Dec. 9, 2019.

Baumgartner et al., Use of a droplet platform to optimize PD-catalyzed C—N coupling reactions promoted by organic bases. Org Proc Res Dev. 2019; 23(8): 1594-1601.

Bourne, Mixing and the selectivity of chemical reactions. Org Proc Res Dev 2013; 7(4): 471-508.

Harris et al., "Velocity profiles in laminar oscillatory flow in tubes," Journal of Physics E: Scientific Instruments 1969, 2(11), 913-916.

Harvey et al., "Operation and optimization of an oscillatory flow continuous reactor," Ind. Eng. Chem. Res. 2001, 40(23), 5371-5377.

Hwang et al., A segmented flow platform for on-demand medicinal chemistry and compound synthesis in oscillating droplets. Chem Commun (Camb). Jun. 16, 2017;53(49):6649-6652.

Mackley et al., Heat Transfer and Associated Energy Dissipation for Oscillatory Flow in Baffled Tubes. Chemical Engineering Science. 1995; 50(14):2211-24.

Mignard et al., Determination of breakage rates of oil droplets in a continuous oscillatory baffled tube. Chemical Engineering Science. 2006; 61:6902-17.

Paquet, Jr., "Tubular reactors for emulsion polymerization: I. Experimental investigation," AIChE J. 1994, 40(1), 73-87.

Zheng et al., The axial dispersion performance of an oscillatory flow meso-reactor with relevance to continuous flow operation. Chemical Engineering Science. 2008; 63:1788-99.

International Search Report and Written Opinion mailed Aug. 3, 2021, for International Application No. PCT/US2021/029522.

Abolhasani et al., Oscillatory three-phase flow reactor for studies of bi-phasic catalytic reactions. Chem Commun (Camb). May 28, 2015;51(43):8916-9.

* cited by examiner

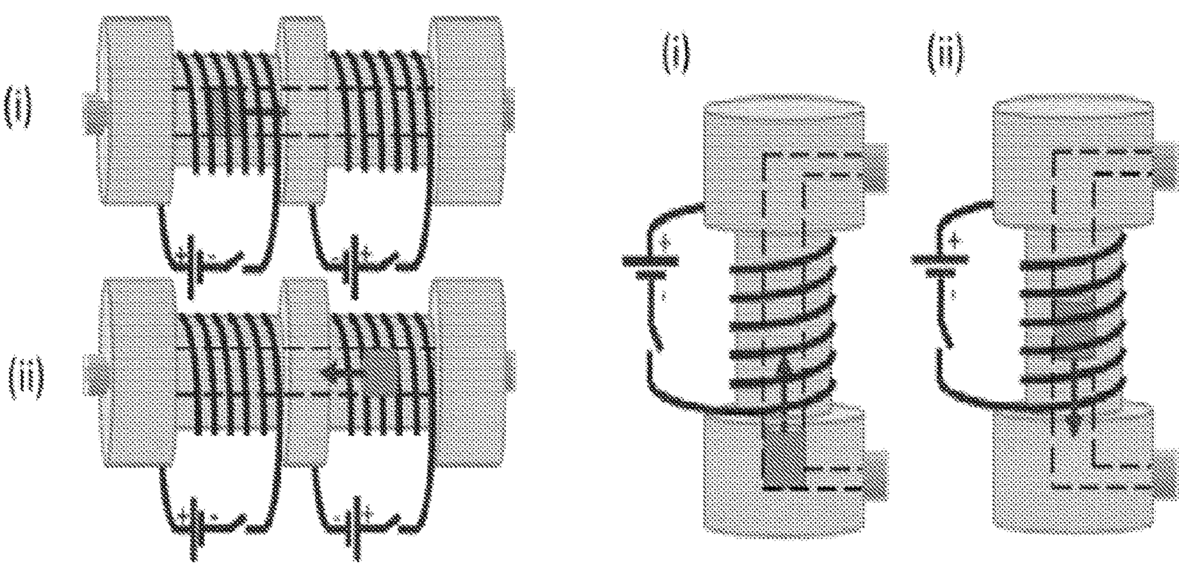
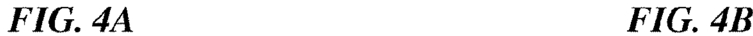
FIG. 4A FIG. 4B
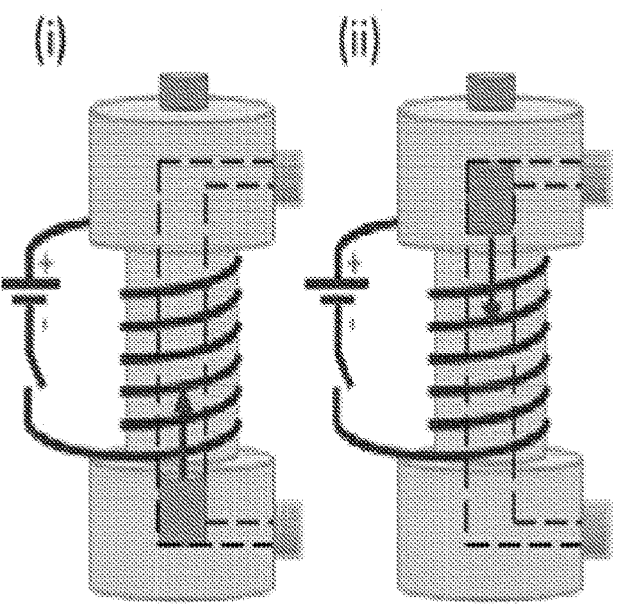
FIG. 4C

ELECTROMECHANICALLY DRIVEN OSCILLATORY FLOW IN FLUIDIC SYSTEMS

RELATED APPLICATIONS

This application is a national stage filing under 35 U.S.C. § 371 of International Patent Application Serial No. PCT/US2021/029522, filed Apr. 28, 2021, and entitled "Electromechanically Driven Oscillatory Flow in Fluidic Systems," which claims priority under 35 U.S.C. § 119 (e) to U.S. Provisional Patent Application No. 63/016,358, filed Apr. 28, 2020, and entitled "Electromechanically Driven Oscillatory Flow in Fluidic Systems," each of which is incorporated herein by reference in its entirety for all purposes.

TECHNICAL FIELD

Fluidic systems and methods in which oscillatory flow is employed are generally described.

SUMMARY

Fluidic systems and methods in which oscillatory flow is employed are generally described. In some instances, one or more solenoids are used to drive the oscillation of a magnetically-susceptible body which creates oscillatory flow of a fluid in a fluidic channel in fluidic communication with a channel containing the magnetically-susceptible body.

The subject matter of the present invention involves, in some cases, interrelated products, alternative solutions to a particular problem, and/or a plurality of different uses of one or more systems and/or articles.

Certain aspects are related to devices. In some embodiments, the device comprises a first fluidic channel; a second fluidic channel; a fluidic loop between and fluidically connected to the first fluidic channel and the second fluidic channel; valving; a magnetically-susceptible body within the fluidic loop; and at least one solenoid associated with the fluidic loop and configured such that, upon application of a voltage to the solenoid, the solenoid generates a magnetic field that causes movement of the magnetically-susceptible body along the fluidic loop. In some embodiments, the valving is configured such that when the valving is in a first position, the valving establishes fluid communication between the first fluidic channel and a first connection of the fluidic loop, and the valving establishes fluid communication between the second fluidic channel and a third connection of the fluidic loop, and when the valving is in a second position, the valving establishes fluid communication between the first connection of the fluidic loop and a second connection of the fluidic loop, and the valving establishes fluid communication between the third connection of the fluidic loop and a fourth connection of the fluidic loop.

In some embodiments, the device comprises a first fluidic channel; a second fluidic channel; a fluidic loop between and fluidically connected to the first fluidic channel and the second fluidic channel; a first valve fluidically connected to the first fluidic channel and the fluidic loop; a second valve fluidically connected to the second fluidic channel and the fluidic loop; a magnetically-susceptible body within the fluidic loop; and at least one solenoid surrounding at least a portion of the fluidic loop and configured such that, upon application of a voltage to the solenoid, the solenoid generates a magnetic field that causes movement of the magnetically-susceptible body along the fluidic loop. In some such embodiments, the first valve is fluidically connected to the first fluidic channel and the fluidic loop such that when the first valve is in a first position, the first valve establishes fluid communication between the first fluidic channel and a first connection of the fluidic loop, and when the first valve is in a second position, the first valve establishes fluid communication between the first connection of the fluidic loop and a second connection of the fluidic loop. In some such embodiments, the second valve is fluidically connected to the second fluidic channel and the fluidic loop such that when the second valve is in a first position, the second valve establishes fluid communication between the second fluidic channel and a third connection of the fluidic loop, and when the second valve is in a second position, the second valve establishes fluid communication between the third connection of the fluidic loop and a fourth connection of the fluidic loop.

In certain embodiments, the device comprises a fluidic channel; a magnetically-susceptible body within the fluidic channel; a magnet comprising a magnetic field that lies at least partially within the fluidic channel; and a solenoid associated with the fluidic channel and configured such that, upon application of a voltage to the solenoid, the solenoid generates a magnetic field that causes movement of the magnetically-susceptible body within the fluidic channel.

Certain aspects are related to methods. In some embodiments, the method comprises transporting a droplet from a first channel of a device into a first portion of a fluidic loop of the device while the device is in a first configuration, wherein, in the first configuration, the first fluidic channel, the first portion of a fluidic loop, and a second fluidic channel are in fluid communication with each other, and a second portion of the fluidic loop is not in fluid communication with any of the first fluidic channel, the first portion of the fluidic loop, and the second fluidic channel. Certain embodiments comprise altering the configuration of the device from the first configuration to a second configuration in which the first portion of a fluidic loop and the second portion of the fluidic loop are in fluid communication with each other, the first fluidic channel is not in fluid communication with the fluidic loop, and the second fluidic channel is not in fluid communication with the fluidic loop. Some embodiments comprise, while the device is in the second configuration, actuating at least one solenoid associated with the fluidic loop to produce oscillatory flow of a magnetically-susceptible body within the fluidic loop.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale unless otherwise indicated. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIGS. 4A-4C are schematic illustrations showing three types of oscillating devices that were developed and tested, in accordance with certain embodiments. FIG. 4A shows a two-solenoid oscillator; FIG. 4B shows a single-solenoid oscillator; and FIG. 4C shows a gravity-balanced oscillator.

DETAILED DESCRIPTION

Figure 1A:
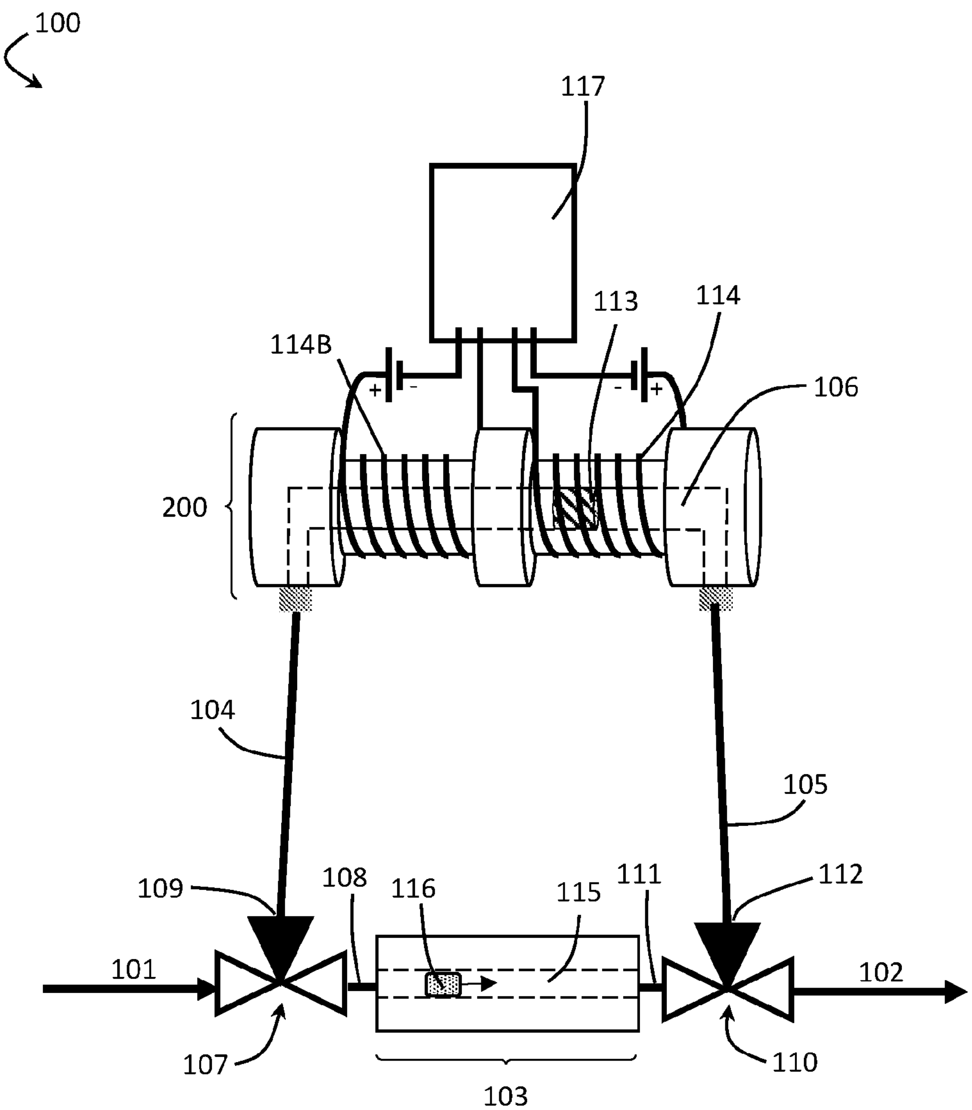
FIGS. 1A-1B are schematic diagrams of a device comprising a magnetically-susceptible body used to generate oscillatory flow, in accordance with certain embodiments.

Fluidic systems and methods in which oscillatory flow is employed are generally described. In some instances, one or more solenoids are used to drive the oscillation of a magnetically-susceptible body which creates oscillatory flow of a fluid in a fluidic channel in fluidic communication with a channel containing the magnetically-susceptible body. In some embodiments, inventive systems comprise a fluidic loop in which the magnetically-susceptible body is positioned. In some embodiments, the system adopts a first configuration (e.g., by adjusting the positions of one or more valves in the system) in which a first portion of the fluidic loop is isolated from a second portion of the fluidic loop that contains the magnetically-susceptible body. This first configuration can be used, for example, to load material into the first portion of the fluidic loop from one or more conduits outside the fluidic loop. In some such embodiments, the system can subsequently adopt a second configuration (e.g., by adjusting the positions of one or more valves in the system) such that in the second configuration, the first portion of the fluidic loop is in fluidic communication with the second portion of the fluidic loop. In the second configuration, the magnetically-susceptible body can be oscillated such that the contents of the first portion of the fluidic loop experience oscillatory flow. The system may be switched between the first configuration and the second configuration multiple times to achieve multiple stages of loading and oscillatory flow.

Certain embodiments are related to fluidic devices. Examples of such devices, in accordance with certain embodiments, are illustrated in FIGS. 1A-1B and 2A-2B.

As shown in FIGS. 1A-1B and FIGS. 2A-2B, device 100 comprises a first fluidic channel 101 and a second fluidic channel 102. In some embodiments, the device comprises a fluidic loop between and fluidically connected to the first fluidic channel and the second fluidic channel. For example, in FIGS. 1A-1B and FIGS. 2A-2B, a fluidic loop is formed in device 100 by first portion 103, fluidic channel 104, fluidic channel 106, and fluidic channel 105.

In some embodiments, first fluidic channel 101 may serve, for example, as an inlet channel (e.g., for loading one or more materials into first portion 103 of the fluidic loop). Second fluidic channel 102 may serve, for example, as an outlet channel (e.g., for removing one or more materials from first portion 103 of the fluidic loop).

As used herein, two elements are in fluidic communication with each other (or, equivalently, in fluid communication with each other) when fluid may be transported from one of the elements to the other of the elements without otherwise altering the configurations of the elements or a configuration of an element between them (such as a valve). Two conduits connected by an open valve (thus allowing for the flow of fluid between the two conduits) are considered to be in fluidic communication with each other. In contrast, two conduits separated by a closed valve (thus preventing the flow of fluid between the conduits) are not considered to be in fluidic communication with each other.

As used herein, two elements are fluidically connected to each other when they are connected such that, under at least one configuration of the elements and any intervening elements, the two elements are in fluidic communication with each other. Two conduits connected by a valve that permits flow between the two conduits in at least one configuration of the valve would be said to be fluidically connected to each other. To further illustrate, two conduits that are connected by a valve that permits flow between the conduits in a first valve configuration but not a second valve configuration are considered to be fluidically connected to each other both when the valve is in the first configuration and when the valve is in the second configuration. In contrast, two fluidic conduits that are not connected to each other (e.g., by a valve, another conduit, or another component) in a way that would permit fluid to be transported between them under any configuration would not be said to be fluidically connected to each other. Elements that are in fluidic communication with each other are always fluidically connected to each other, but not all elements that are fluidically connected to each other are necessarily in fluidic communication with each other.

In certain embodiments, the system comprises valving. The valving may include one or more valves that can be actuated to adjust the flow of fluid through the system.

Figure 2A:
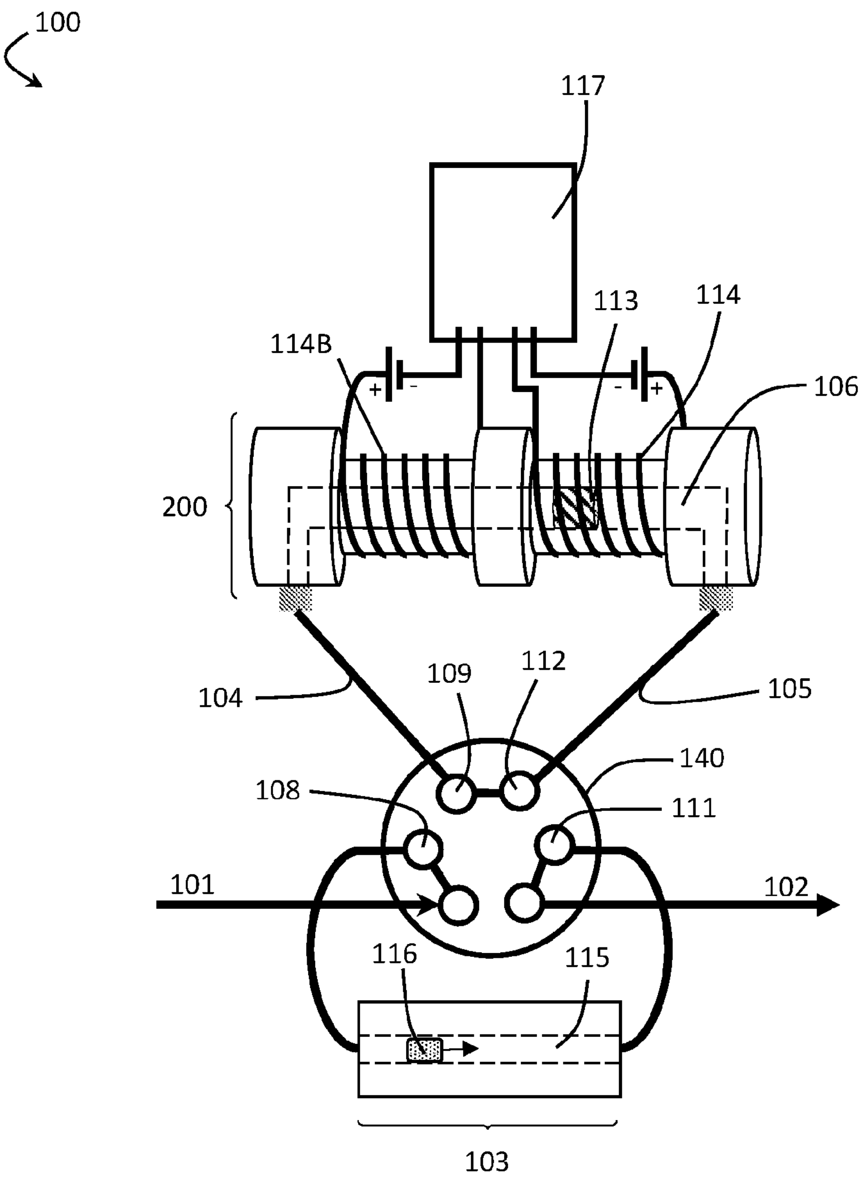
FIGS. 2A-2B are schematic diagrams of a device comprising a magnetically-susceptible body used to generate oscillatory flow in a system comprising a six-way valve, in accordance with certain embodiments.

In some embodiments, the valving is configured such that, when the valving is in a first position, the valving establishes fluid communication between the first fluidic channel and a first connection of the fluidic loop, and the valving establishes fluid communication between the second fluidic channel and a third connection of the fluidic loop. One example of such an arrangement (in a system comprising two three-way valves) is shown in FIG. 1A and is explained in more detail below. Another example of such an arrangement (in a system comprising one six-way valve) is shown in FIG. 2A and is also explained in more detail below.

Figure 1B:
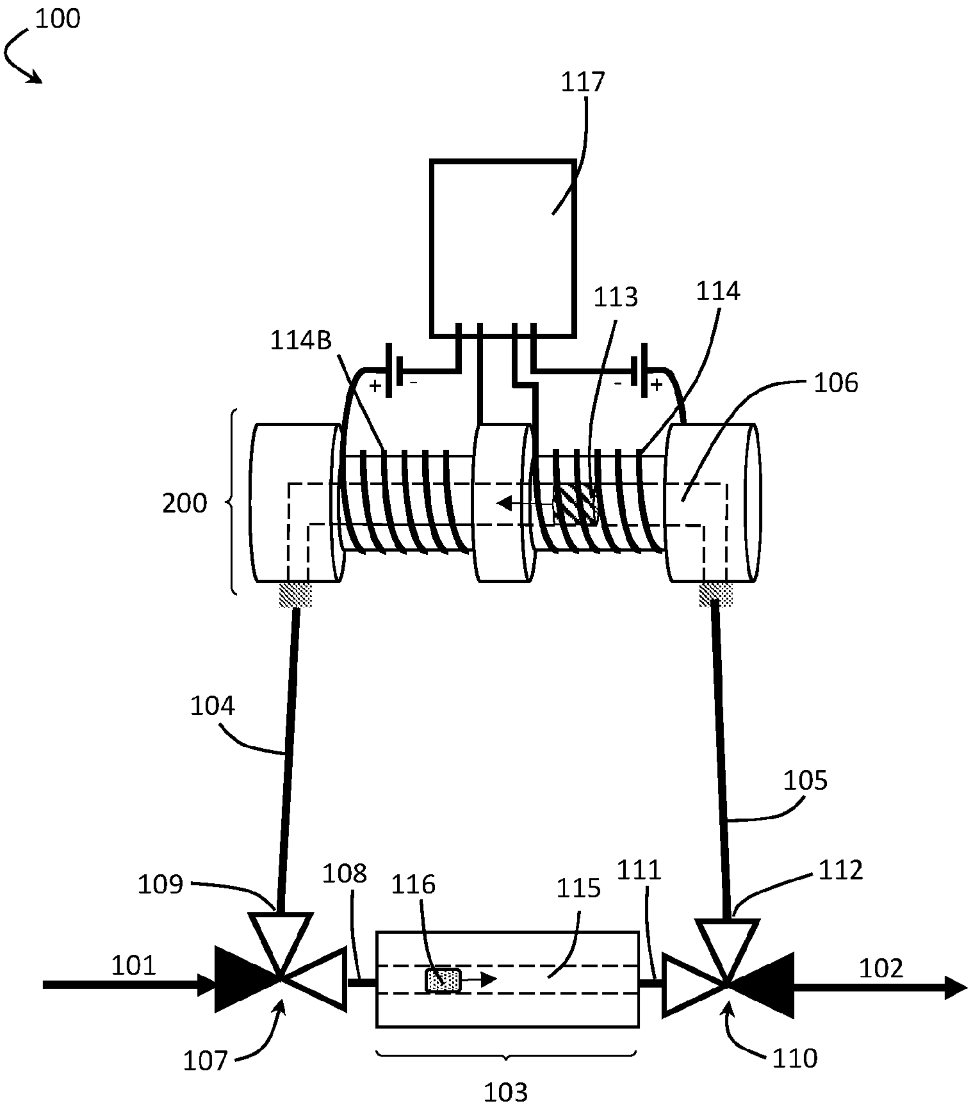
Figure 2B:
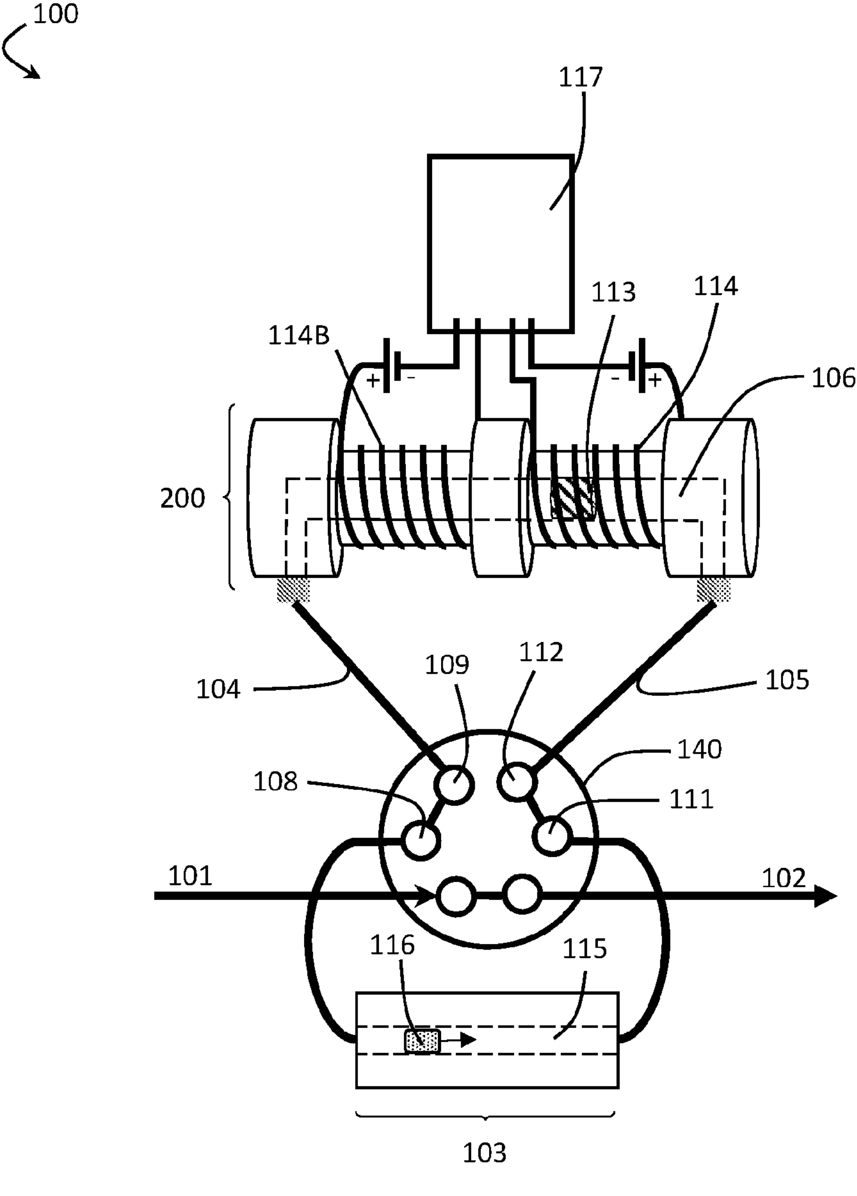

In certain embodiments, the valving is configured such that, when the valving is in a second position, the valving establishes fluid communication between the first connection of the fluidic loop and a second connection of the fluidic loop, and the valving establishes fluid communication between the third connection of the fluidic loop and a fourth connection of the fluidic loop. One example of such an arrangement (in a system comprising two three-way valves) is shown in FIG. 1B and is explained in more detail below. Another example of such an arrangement (in a system comprising one six-way valve) is shown in FIG. 2B and is also explained in more detail below.

A first set of embodiments in which the valving comprises two three-way valves, as illustrated in FIGS. 1A-1B, is now described.

As noted above, in some embodiments, the system comprises a first valve. For example, in FIGS. 1A-1B, device 100 comprises first valve 107, which is illustrated as a three-way valve. First valve 107 is fluidically connected to first fluidic channel 101, first connection 108 of the fluidic loop (a fluidic connection between the valve and first portion 103 of the fluidic loop), and second connection 109 of the fluidic loop (a fluidic connection between the valve and fluidic channel 104, which is part of the second portion of the fluidic loop).

The system can also comprise, in some embodiments, a second valve. For example, in FIGS. 1A-1B, device 100 comprises second valve 110, which is also illustrated as a three-way valve. Second valve 110 is fluidically connected to second fluidic channel 102, third connection 111 of the fluidic loop (a fluidic connection between the valve and first portion 103 of the fluidic loop), and fourth connection 112 of the fluidic loop (a fluidic connection between the valve and fluidic channel 105, which is part of the second portion of the fluidic loop).

In FIGS. 1A-1B, black triangles are used to indicate closed connections of a valve and white triangles are used to indicate open connections of a valve.

In some embodiments, the first valve is fluidically connected to the first fluidic channel and the fluidic loop such that when the first valve is in a first position, the first valve establishes fluidic communication between the first fluidic channel and a first connection of the fluidic loop. The first connection of the fluidic loop can be a connection between the valve and the first portion of the fluidic loop. An example of this arrangement is shown in FIG. 1A. In FIG. 1A, first valve 107 is in a first position in which it establishes fluidic communication between first fluidic channel 101 and first connection 108 of the fluidic loop. In some such embodiments, when the first valve is in the first position, the first fluidic channel and the first portion of the fluidic loop can be in fluidic communication. For example, in FIG. 1A, first fluidic channel 101 is illustrated as being in fluidic communication with first portion 103 of the fluidic loop. This configuration can allow, for example, for the transport of material from first fluidic channel 101 to first portion 103 of the fluidic loop (e.g., during a phase in which new material is loaded into the fluidic loop via first portion 103).

In some embodiments, the second valve is fluidically connected to the second fluidic channel and the fluidic loop such that when the second valve is in a first position, the second valve establishes fluidic communication between the second fluidic channel and a third connection of the fluidic loop. The third connection of the fluidic loop can be a connection between the valve and the first portion of the fluidic loop. An example of this arrangement is shown in FIG. 1A. In FIG. 1A, second valve 110 is in a first position in which it establishes fluidic communication between second fluidic channel 102 and third connection 111 of the fluidic loop. In some such embodiments, when the second valve is in the first position, the second fluidic channel and the first portion of the fluidic loop can be in fluidic communication. For example, in FIG. 1A, second fluidic channel 102 is illustrated as being in fluidic communication with first portion 103 of the fluidic loop. This configuration can allow, for example, for the transport of material out of the first portion 103 of the fluidic loop via second fluidic channel 102 (e.g., during a phase in which material is removed from the fluidic loop via first portion 103).

In some embodiments, the first and second valves can be in their respective "first positions" at the same time (and, together, the first and second valves being in their respective "first positions" can be part of a first position of the valving of the system as a whole). By arranging the valves in this way, new material can be loaded into first portion 103 of the fluidic loop, while the second portion of the fluidic loop is fluidically isolated.

In some embodiments, the first valve is fluidically connected to the first fluidic channel and the fluidic loop such that when the first valve is in a second position, the first valve establishes fluidic communication between the first connection of the fluidic loop and a second connection of the fluidic loop. The second connection of the fluidic loop can be a connection between the valve and the second portion of the fluidic loop. An example of this arrangement is shown in FIG. 1B. In FIG. 1B, first valve 107 is in a second position in which it establishes fluidic communication between first connection 108 of the fluidic loop and second connection 109 of the fluidic loop. In some such embodiments, when the first valve is in the second position, the first portion of the fluidic loop and the second portion of the fluidic loop can be in fluidic communication. For example, in FIG. 1B, first portion 103 of the fluidic loop is illustrated as being in fluidic communication with fluidic channel 104 (which is part of the second portion of the fluidic loop) via first valve 107. This configuration can allow, for example, oscillatory flow in the second portion of the fluidic loop to create oscillatory flow within the first portion of the fluidic loop.

In some embodiments, the second valve is fluidically connected to the second fluidic channel and the fluidic loop such that when the second valve is in a second position, the second valve establishes fluidic communication between the third connection of the fluidic loop and a fourth connection of the fluidic loop. The fourth connection of the fluidic loop can be a connection between the valve and the second portion of the fluidic loop. An example of this arrangement is shown in FIG. 1B. In FIG. 1B, second valve 110 is in a second position in which it establishes fluidic communication between third connection 111 of the fluidic loop and fourth connection 112 of the fluidic loop. In some such embodiments, when the second valve is in the second position, the first portion of the fluidic loop and the second portion of the fluidic loop can be in fluid communication. For example, in FIG. 1B, first portion 103 of the fluidic loop is illustrated as being in fluidic communication with fluidic channel 105 (which is part of the second portion of the fluidic loop). This configuration can allow, for example, oscillatory flow in the second portion of the fluidic loop to create oscillatory flow within the first portion of the fluidic loop.

In some embodiments, the first and second valves can be in their respective "second positions" at the same time (and, together, the first and second valves being in their respective "second positions" can be part of a second position of the valving of the system as a whole). By arranging the valves in this way, establishing oscillatory flow in the second portion of the fluidic loop can also establish oscillatory flow within the first portion of the fluidic loop. In addition, in this configuration, material within the fluidic loop can be subjected to oscillatory flow without leaking material out of and/or into the fluidic loop.

As noted above, the use of multiple valves is not required, and in some embodiments, a single valve can be used. FIGS. 2A-2B illustrate a set of embodiments in which a single six-way valve is used to adjust the flow of fluid through the system. In FIGS. 2A-2B, device 100 comprises valve 140, which is illustrated as a six-way valve. Valve 140 is fluidically connected to first fluidic channel 101, first connection 108 of the fluidic loop (a fluidic connection between the valve and first portion 103 of the fluidic loop), second connection 109 of the fluidic loop (a fluidic connection between the valve and fluidic channel 104, which is part of the second portion of the fluidic loop), second fluidic channel 102, third connection 111 of the fluidic loop (a fluidic connection between the valve and first portion 103 of the fluidic loop), and fourth connection 112 of the fluidic loop (a fluidic connection between the valve and fluidic channel 105, which is part of the second portion of the fluidic loop).

In some embodiments, the valve is fluidically connected to the first fluidic channel and the fluidic loop such that when the valve is in a first position, the valve establishes fluidic communication between the first fluidic channel and a first connection of the fluidic loop. The first connection of the fluidic loop can be a connection between the valve and the first portion of the fluidic loop. An example of this arrangement is shown in FIG. 2A. In FIG. 2A, valve 140 is in a first position in which it establishes fluidic communication between first fluidic channel 101 and first connection 108 of the fluidic loop. In some such embodiments, when the valve is in the first position, the first fluidic channel and the first portion of the fluidic loop can be in fluidic communication. For example, in FIG. 2A, first fluidic channel 101 is illustrated as being in fluidic communication with first portion 103 of the fluidic loop. This configuration can allow, for example, for the transport of material from first fluidic channel 101 to first portion 103 of the fluidic loop (e.g., during a phase in which new material is loaded into the fluidic loop via first portion 103).

In some embodiments, the valve is also fluidically connected to the second fluidic channel and the fluidic loop such that when the valve is in a first position, the valve establishes fluidic communication between the second fluidic channel and a third connection of the fluidic loop. The third connection of the fluidic loop can be a connection between the valve and the first portion of the fluidic loop. An example of this arrangement is shown in FIG. 2A. In FIG. 2A, valve 140, while in its first position, establishes fluidic communication between second fluidic channel 102 and third connection 111 of the fluidic loop. In some such embodiments, when the valve is in the first position, the second fluidic channel and the first portion of the fluidic loop can be in fluidic communication. For example, in FIG. 2A, second fluidic channel 102 is illustrated as being in fluidic communication with first portion 103 of the fluidic loop. This configuration can allow, for example, for the transport of material out of the first portion 103 of the fluidic loop via second fluidic channel 102 (e.g., during a phase in which material is removed from the fluidic loop via first portion 103).

In some embodiments, the valve is fluidically connected to the first fluidic channel and the fluidic loop such that when the valve is in a second position, the valve establishes fluidic communication between the first connection of the fluidic loop and a second connection of the fluidic loop. The second connection of the fluidic loop can be a connection between the valve and the second portion of the fluidic loop. An example of this arrangement is shown in FIG. 2B. In FIG. 2B, valve 140 is in a second position in which it establishes fluidic communication between first connection 108 of the fluidic loop and second connection 109 of the fluidic loop. In some such embodiments, when the valve is in the second position, the first portion of the fluidic loop and the second portion of the fluidic loop can be in fluidic communication. For example, in FIG. 2B, first portion 103 of the fluidic loop is illustrated as being in fluidic communication with fluidic channel 104 (which is part of the second portion of the fluidic loop) via valve 140. This configuration can allow, for example, oscillatory flow in the second portion of the fluidic loop to create oscillatory flow within the first portion of the fluidic loop.

In some embodiments, the valve is fluidically connected to the second fluidic channel and the fluidic loop such that when the valve is in its second position, the valve establishes fluidic communication between the third connection of the fluidic loop and a fourth connection of the fluidic loop. The fourth connection of the fluidic loop can be a connection between the valve and the second portion of the fluidic loop. An example of this arrangement is shown in FIG. 2B. In FIG. 2B, valve 140, in its second position, establishes fluidic communication between third connection 111 of the fluidic loop and fourth connection 112 of the fluidic loop. In some such embodiments, when the valve is in the second position, the first portion of the fluidic loop and the second portion of the fluidic loop can be in fluid communication. For example, in FIG. 2B, first portion 103 of the fluidic loop is illustrated as being in fluidic communication with fluidic channel 105 (which is part of the second portion of the fluidic loop). This configuration can allow, for example, oscillatory flow in the second portion of the fluidic loop to create oscillatory flow within the first portion of the fluidic loop.

In some embodiments, the device comprises a magnetically-susceptible body. In FIGS. 1A-1B and FIGS. 2A-2B, device 100 comprises magnetically-susceptible body 113. The magnetically-susceptible body can be positioned, in some embodiments, within the fluidic loop. For example, in FIGS. 1A-1B and FIGS. 2A-2B, magnetically-susceptible body 113 is positioned within fluidic channel 106 of the fluidic loop (which is shown as being within region 200 in FIGS. 1A-1B and FIGS. 2A-2B).

In certain embodiments, the device comprises at least one solenoid surrounding at least a portion of the fluidic loop. For example, in FIGS. 1A-1B and FIGS. 2A-2B, region 200 of device 100 comprises solenoid 114 and optional solenoid 114B surrounding portions of fluidic channel 106 of the fluidic loop. While FIGS. 1A-1B and FIGS. 2A-2B show two solenoids within region 200, other embodiments may make use of a different number of solenoids (e.g., a single solenoid, or more than two solenoids). Examples of such systems are described in more detail below.

In some embodiments, the magnetically-susceptible body and the at least one solenoid can be used to generate oscillatory flow. For example, in certain embodiments, the at least one solenoid can be configured such that, upon application of a voltage to the solenoid, the solenoid generates a magnetic field that causes movement (e.g., oscillatory movement) of the magnetically-susceptible body along the fluidic loop. For example, in FIGS. 1A-1B and FIGS. 2A-2B, in some embodiments, application of a voltage to solenoid 114 (and, optionally, to solenoid 114B) generates a magnetic field that causes movement (e.g., oscillatory movement) of magnetically-susceptible body 113 within fluidic channel 106.

In some embodiments, the solenoid(s) is configured such that application of the voltage results in the magnetically-susceptible body being repelled by the solenoid, while in other embodiments, the solenoid(s) is configured such that application of the voltage results in the magnetically-susceptible body being attracted to the solenoid. Those of ordinary skill in the art, given the guidance provided by the present disclosure, would be capable of arranging the solenoids and the magnetically-susceptible body to achieve the desired movement of the magnetically-susceptible body.

Figure 3A:
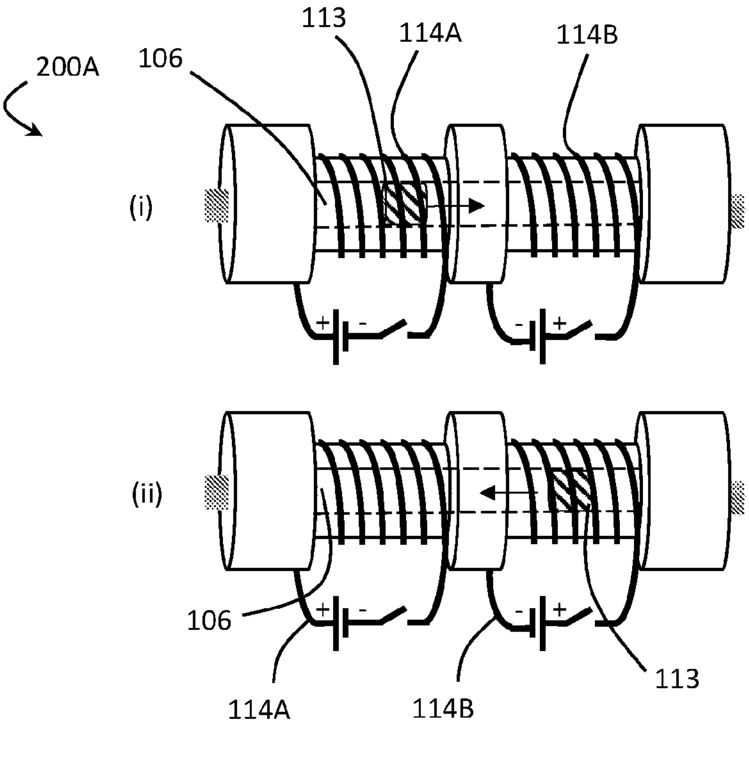
FIGS. 3A-3C are, in accordance with some embodiments, schematic illustrations showing various configurations of devices in which a magnetically-susceptible body is used to generate oscillatory flow.

As noted above, the oscillatory flow can be established within region 200 in a variety of ways. In some embodiments, the device comprises a first solenoid and a second solenoid configured such that oscillatory flow of the magnetically-susceptible body is produced by applying alternating voltages between the first solenoid and the second solenoid. An example of this type of arrangement is shown, for example in FIG. 3A (and is similar to the arrangement shown in FIGS. 1A-1B and FIGS. 2A-2B). In FIG. 3A, region 200A comprises first solenoid 114A and second solenoid 114B. First solenoid 114A and second solenoid 114B can be configured such that oscillatory flow of magnetically-susceptible body 113 is produced by applying alternating voltages between first solenoid 114A and second solenoid 114B. For example, in some embodiments, a voltage can be applied to solenoid 114A; subsequently, a voltage can be applied to solenoid 114B while the voltage is no longer applied to solenoid 114A; subsequently, a voltage can be applied, again, to solenoid 114A while the voltage is no longer applied to solenoid 114B; and so on.

Figure 3B:
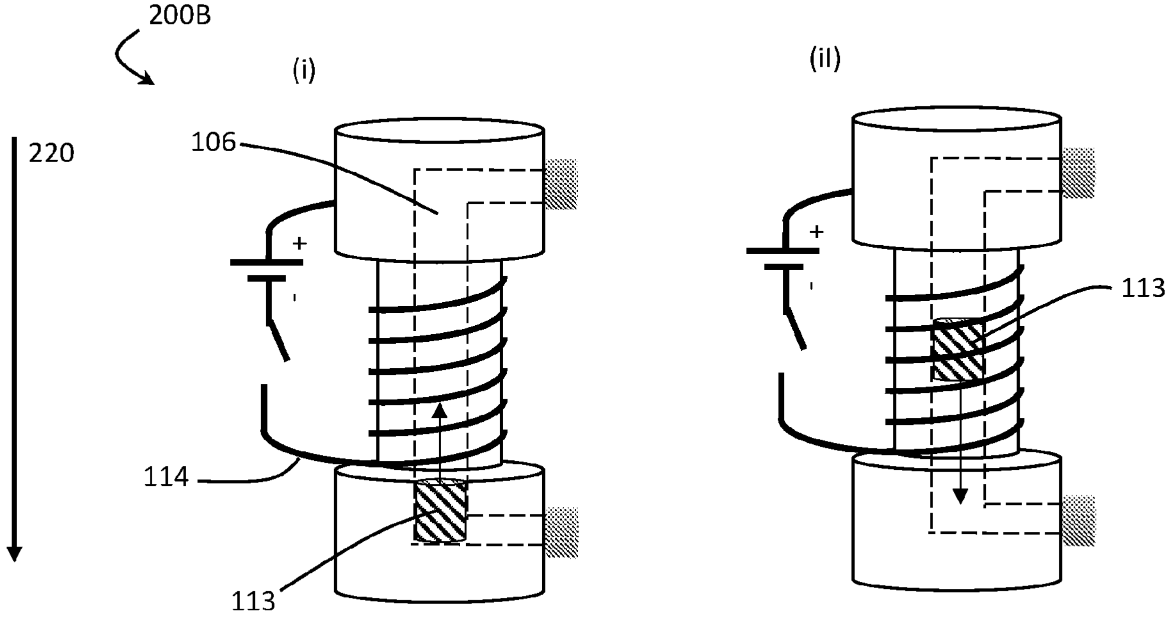

In some embodiments, a single solenoid is configured such that oscillatory flow of the magnetically-susceptible body is produced by applying a voltage to the solenoid to transport the magnetically-susceptible body against the force of gravity and removing the applied voltage to allow the magnetically-susceptible body to move with the force of gravity. One example of such an arrangement is shown in FIG. 3B. In FIG. 3B, region 200B includes a single solenoid 114. Solenoid 114 is configured such that oscillatory flow of the magnetically-susceptible body is produced by applying a voltage to solenoid 114 to transport magnetically-susceptible body 113 upward, against the force of gravity, which is illustrated using arrow 220 in in FIG. 3B. Subsequently, the applied voltage can be removed from solenoid 114 to allow magnetically-susceptible body 113 to move downward, with the force of gravity. This process can be repeated to produce oscillatory flow within fluidic channel 106 of region 200B.

Figure 3C:
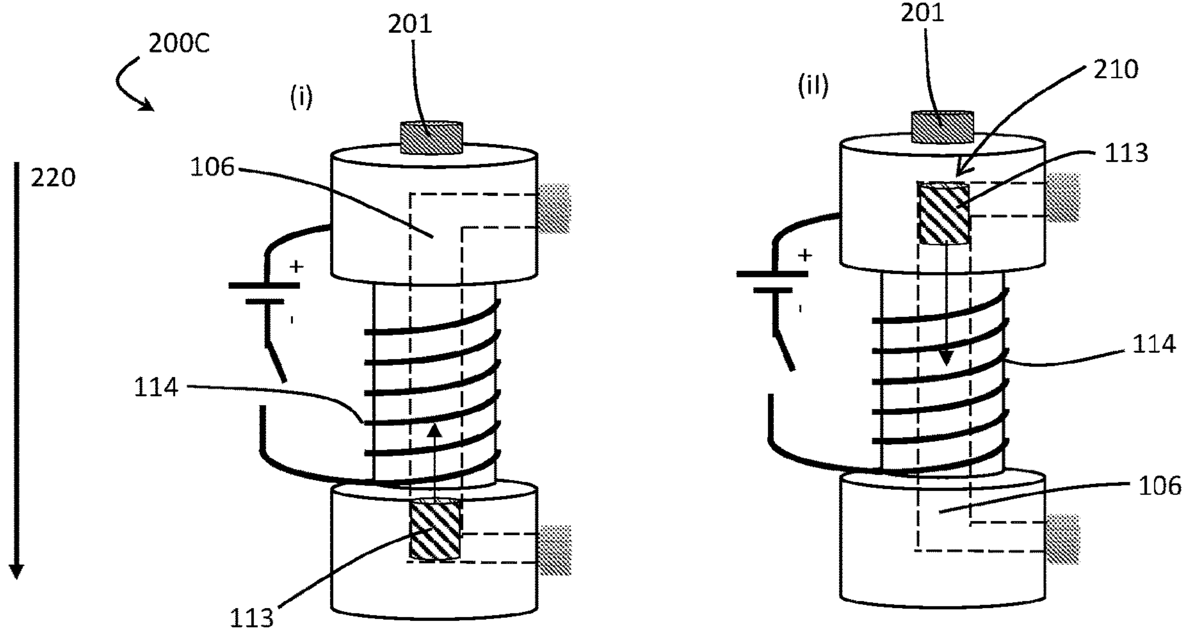

In some embodiments, the device further comprises a magnet adjacent to the fluidic loop. In some such embodiments, the magnet and a single solenoid are configured such that oscillatory flow of the magnetically-susceptible body is produced by applying a first voltage to the solenoid to transport the magnetically-susceptible body against the force of gravity and toward the magnet, and applying a second voltage to the solenoid to transport the magnetically-susceptible body with the force of gravity and away from the magnet. One example of such an arrangement is shown in FIG. 3C. In FIG. 3C, region 200C comprises fluidic channel 106, magnetically-susceptible body 113 within fluidic channel 106, magnet 201, and solenoid 114. Magnet 201 comprises a magnetic field that lies at least partially within fluidic channel 106. In some embodiments, the solenoid surrounds at least a portion of the fluidic channel and is configured such that, upon application of a voltage to the solenoid, the solenoid generates a magnetic field that causes movement of the magnetically-susceptible body within the fluidic channel. For example, referring to FIG. 3C, solenoid 114 surrounds at least a portion of fluidic channel 106 and is configured such that, upon application of a voltage to solenoid 114, solenoid 114 generates a magnetic field that causes movement of magnetically-susceptible body 113 within fluidic channel 106. In the left-hand side of FIG. 3C, for example, the application of a voltage to solenoid 114 can cause magnetically-susceptible body 113, originally positioned below solenoid 114, to be projected upward toward magnet 201. The magnetic field of magnet 201 can hold magnetically-susceptible body 113 against the top of fluidic channel 106 (shown by arrow 210 in FIG. 3C), against the force of gravity. In some such embodiments, magnetically-susceptible body 113 can remain in place until a voltage is again applied to solenoid 114, which can result in the movement of magnetically-susceptible body 113 away from magnet 201 (in this case, downward, with the force of gravity). This process can be repeated to create oscillatory flow within fluidic channel 106.

In certain embodiments, the oscillatory transport of the magnetically-susceptible body can be controlled or otherwise adjusted using a controller. For example, in FIGS. 1A-1B and FIGS. 2A-2B, controller 117 can be used to control or otherwise adjust the oscillation of magnetically-susceptible body 113. This, in turn, may lead to the ability to control or otherwise adjust the oscillatory flow to which droplet 116 is subjected. Any of a variety of controllers can be used for this purpose, including any of a variety of computer-implemented controllers known to those of skill in the art.

Certain aspects are related to methods of operating fluidic devices. In some embodiments, the method comprises transporting a droplet from a first channel of a device into a first portion of a fluidic loop of a device while the device is in a first configuration. For example, referring to FIG. 1A, droplet 116 can be transported from first fluidic channel 101 into first portion 103 of the fluidic loop while device 100 is in the first configuration illustrated in FIG. 1A (in which device 100 may have any of the features and properties described above with respect to the first configuration). Similar droplet transport can be performed using device 100 in FIG. 2A. In some such embodiments, in the first configuration, the first fluidic channel, the first portion of the fluidic loop, and the second fluidic channel are in fluidic communication with each other. For example, in FIGS. 1A and 2A, first fluidic channel 101, first portion 103 of the fluidic loop, and second fluidic channel 102 are in fluidic communication with each other. In some such embodiments, the second portion of the fluidic loop is not in fluidic communication with any of the first fluidic channel, the first portion of the fluidic loop, and the second fluidic channel. For example, as shown in FIGS. 1A and 2A, the second portion of the fluidic loop (which includes fluidic channel 104, fluidic channel 105 and fluidic channel 106) is not in fluidic communication with any of first fluidic channel 101, first portion 103 of the fluidic loop, and second fluidic channel 102.

Certain embodiments comprise altering the configuration of the device from the first configuration to a second configuration. This can be achieved, for example, by actuating valving of the system (which may, as described above, include one or more valves). To illustrate, FIG. 1A shows device 100 in a first configuration in which first valve 107 and second valve 110 have been actuated to establish fluidic communication between first fluidic channel 101, first portion 103 of the fluidic loop, and second fluidic channel 102. FIG. 1B shows device 100 in a second configuration in which first valve 107 and second valve 110 have been actuated to establish fluidic communication between first portion 103 of the fluidic loop and the second portion of the fluidic loop (which includes fluidic channel 104, fluidic channel 105, and fluidic channel 106). As another example, FIG. 2A shows device 100 in a first configuration in which valve 140 has been actuated to establish fluidic communication between first fluidic channel 101, first portion 103 of the fluidic loop, and second fluidic channel 102. FIG. 2B shows device 100 in a second configuration in which valve 140 has been actuated to establish fluidic communication between first portion 103 of the fluidic loop and the second portion of the fluidic loop (which includes fluidic channel 104, fluidic channel 105, and fluidic channel 106).

In some embodiments, in the second configuration, the first portion of a fluidic loop and the second portion of the fluidic loop are in fluidic communication with each other. For example, as noted above, one such configuration is illustrated in FIG. 1B. Another such configuration is illustrated in FIG. 2B. In some embodiments, in the second configuration, the first fluidic channel is not in fluidic communication with the fluidic loop, and the second fluidic channel is not in fluidic communication with the fluidic loop. For example, in FIG. 1B, first fluidic channel 101 is not in fluidic communication with the fluidic loop (which includes first portion 103, fluidic channel 104, fluidic channel 105, and fluidic channel 106, all of which are in fluidic communication with each other in FIG. 1B), and second fluidic channel 102 is not in fluidic communication with the fluidic loop. As another example, in FIG. 2B, first fluidic channel 101 is not in fluidic communication with the fluidic loop (which includes first portion 103, fluidic channel 104, fluidic channel 105, and fluidic channel 106, all of which are in fluidic communication with each other in FIG. 2B), and second fluidic channel 102 is not in fluidic communication with the fluidic loop.

Certain embodiments comprise, while the device is in the second configuration, actuating at least one solenoid associated with the fluidic loop to produce oscillatory flow of a magnetically-susceptible body within the fluidic loop. For example, in some embodiments, while device 100 is in the configuration shown in FIG. 1B and/or the configuration shown in FIG. 2B, solenoid 114 (and, optionally, solenoid 114B) can be actuated to produce oscillatory flow of magnetically-susceptible body 113 within the fluidic loop. Other solenoid-driven oscillatory flow mechanisms could also be used, including those illustrated in FIGS. 3A-3C.

In certain embodiments, the oscillatory flow can have a relatively high frequency. For example, in some embodiments, the oscillatory flow can have a frequency of at least 1 Hz, at least 10 Hz, at least 50 Hz, or at least 95 Hz. In some embodiments, the oscillatory flow can have a frequency of less than or equal to 200 Hz, or less than or equal to 100 Hz. In some embodiments, the frequency of the oscillatory flow can be adjusted (e.g., continuously adjusted) such that the oscillation frequency may be at any frequency greater than 0 Hz and up to 100 Hz.

In some embodiments, the fluidic loop can comprise and/or be a reactor. For example, referring back to FIGS. 1A-1B and FIGS. 2A-2B, in some embodiments, first portion 103 of the fluidic loop can be or comprise a reactor 115. In some such embodiments, the fluidic channel within which oscillatory motion of the magnetically-susceptible body is produced can be fluidically connected to the reactor. The system can include one or more valves that allow one to establish fluidic communication between the reactor and the fluidic channel within which oscillatory motion of the magnetically-susceptible body is produced, which can allow one to establish oscillatory flow within the reactor by oscillating the magnetically-susceptible body.

In some embodiments, the reactor can comprise a droplet of fluid (e.g., a liquid within a liquid stream, a liquid within a gaseous stream, or a gas within a liquid stream).

Any of a variety of materials can be used as the magnetically-susceptible body. Generally, the magnetically-susceptible body will be made of a material (whether in pure or composite form) such that the magnetically-susceptible body moves in response to an applied magnetic field. Permanent or non-permanent magnetic material can be used.

The magnetically-susceptible body can also take on any of a variety of suitable phases. In some embodiments, the magnetically-susceptible body is a solid body. In certain embodiments, the magnetically-susceptible body comprises a magnetically-susceptible fluid, such as a ferrofluid. In some such embodiments, the magnetically-susceptible fluid can be enclosed within a solid container, while in other such embodiments, the magnetically-susceptible fluid can be confined via immiscibility with a surrounding fluid. Examples of magnetically-susceptible material include, but are not limited to, iron-containing materials (including materials containing elemental iron, oxides of iron, or any other iron-containing material, such as magnetite ($Fe_3O_4$)), permanent magnets (e.g., magnets comprising iron, nickel, cobalt, rare earth metals such as neodymium, praseodymium, samarium, gadolinium, and dysprosium), naturally-occurring minerals (e.g., lodestone), and/or alloys, composites, or other mixtures of these.

Any of a variety of fluids can be subjected to oscillatory flow using various of the embodiments described herein. In some embodiments, the fluid within the fluidic loop is gaseous (e.g., comprising a pure gas or a mixture of two or more gases). In some embodiments, the fluidic loop contains a liquid (e.g., a pure liquid, a combination of two or more liquids, and/or a combination of one or more liquids with a non-liquid such as one or more gases and/or one or more solids). In some embodiments, one or more solids may be suspended or otherwise contained within the fluid as might be present, for example, in a suspension or other flowable material that includes a solid. In some embodiments, the fluidic loop contains a liquid-containing droplet that is present within another liquid that is immiscible with the liquid phase of the liquid-containing droplet. In some embodiments, the fluidic loop contains a gas-containing droplet that is present within a liquid phase within the fluidic loop.

In some embodiments, the systems and methods described herein can be used to provide flow during relatively long residence times (e.g., at least 24 hours, at least 48 hours, at least 7 days, or longer) without the need for large lengths of conduit.

In some embodiments, the systems and methods described herein can be used to generate oscillatory flow (e.g., at any of the frequencies mentioned elsewhere herein) using pressures of less than 80 psi.

In some embodiments, certain of the devices described herein may comprise components with small length scales (e.g., centimeter, millimeter, micrometer) and/or form at least a part of an apparatus comprising a small length scale component. For instance, in some embodiments, the device may form at least a part of a millifluidic apparatus. As used herein, a millifluidic apparatus contains at least one fluidic channel having a minimum cross-sectional diameter of less than 1 centimeter (and, in some embodiments, less than 100 millimeters or less than 10 millimeters). In some embodiments, the millifluidic apparatus contains at least one fluidic channel having a maximum cross-sectional diameter of less than 1 centimeter (or less than 100 millimeters, or less than 10 millimeters). In some instances, the device forms at least a part of a microfluidic apparatus. As used, herein, a microfluidic apparatus contains at least one channel having a minimum cross-sectional diameter of less than 1 millimeter (and, in some embodiments, less than 100 micrometers or less than 10 micrometers). In some embodiments, the microfluidic apparatus contains at least one fluidic channel having a maximum cross-sectional diameter of less than 1 millimeter (or less than 100 micrometers, or less than 10 micrometers). In some embodiments, the device itself can be a millifluidic apparatus or a microfluidic apparatus. It should be understood, however, that the present disclosure is not limited to such small-scale systems, and in other embodiments, larger scale channels and other system components may be used.

U.S. Provisional Patent Application No. 63/016,358, filed Apr. 28, 2020, and entitled "Electromechanically Driven Oscillatory Flow in Fluidic Systems" is incorporated herein by reference in its entirety for all purposes.

The following example is intended to illustrate certain embodiments of the present invention, but does not exemplify the full scope of the invention.

EXAMPLE

This example describes the design and development of a device for the generation of oscillatory flow in fluidic systems. In some cases, the systems can be microfluidic systems. In some embodiments, the system can be parallelized to allow for the scale-up of the amount of fluid processed by the system.

Automated synthesis platforms are a central step toward high-throughput experimentation in the chemical sciences and exhibit great potential, especially in drug discovery and development in the pharmaceutical industry. The application of alternating pressure to induce oscillation of a microdroplet of reacting material is described in U.S. Pat. No. 10,252,239 ("the '239 Patent"), which is incorporated herein by reference in its entirety for all purposes. It was discovered, however, that the mechanism used to achieve alternating pressure in the platform described in the '239 Patent is not readily parallelizable, which has inhibited the use of that platform for high-throughput experimentation.

Various embodiments of the devices described in this example can provide one or more of a variety of advantages including, but not limited to the following:

In certain embodiments, the device generates stable oscillations by design. That is to say, the resting positions of an oscillating droplet, in accordance with certain embodiments, do not shift over time. This provides access to theoretically infinite oscillation periods without reliance on droplet position tracking. In contrast, existing methods generally require optical tracking of the droplet to prevent these shifts.

The device provides, in some embodiments, access to larger flow rates and Reynolds numbers than current methods. Flow rates can be controlled via operational variables and hardware configuration, providing access to a wide range of flow rates inside the laminar regime. Oscillation under turbulent conditions has also been shown, although its use may potentially be limited due to microdroplet breakup.

In accordance with certain embodiments, the design of the device allows for parallelization, providing access to parallelized high-throughput automated synthesis platforms.

The functionality of the device can be made to be independent of scale. This can allow for upscaling (i.e., larger devices that can create larger displacements). While existing technologies also scale to some degree, this technology eases the use of oscillatory flow at larger scales beyond the microliter range.

In accordance with certain embodiments, the device can achieve a wide range of oscillation frequencies. Tight control over frequency can be achieved, for example, through control of operational variables. Frequencies up to 24 Hz and higher have been demonstrated. In certain embodiments, oscillation frequencies of up to 100 Hz can be achieved. The ability to create high frequencies is desirable. As one example, the use of high frequencies can allow for rapid mixing in droplets, which can allow for more reproducible handling of mixing-sensitive reactions (such as liquid-liquid and solid-liquid reaction mixtures) as well as higher conversions. In addition, in certain embodiments, the system can be controlled such that the frequency can be continuously varied within a particular range. In addition, in some embodiments, the frequency can be decoupled from displacement.

There is a wide range of use cases for various of the embodiments described herein. In general, the devices may be operated both in gaseous and liquid systems and at different pressure levels, providing a wide range of possible applications in microfluidics. In some embodiments, the device can be used to generate oscillatory flow in a parallelized version of an automated synthesis platform. Other applications arise in the general field of microfluidics. Generally, oscillatory flow is an emerging technology with a variety of applications. In some cases, the oscillatory flow may be used in platforms for the measurement of reaction and enzyme kinetics, the measurement of octanol-water partition coefficients, and the sorting of microparticles based on size. The ability to 1) generate stable oscillations without droplet shifting or reliance on droplet tracking and 2) readily adjust both oscillation displacement volume and frequency can make these systems very desirable for use in a wide variety of oscillatory flow applications.

Three different versions of the device are shown in FIGS. 4A-4C. All three designs have been shown to generate stable, long-term oscillations at a wide range of displacements and frequencies. Each design offers unique benefits.

The two-solenoid oscillator (FIG. 4A) includes two solenoids wrapped around a housing (e.g., a fluoropolymer housing) containing a hollow core with a magnet inside. By supplying current to one solenoid, the magnet is accelerated toward the second solenoid. The single-solenoid oscillator (FIG. 4B) leverages gravity. When the solenoid is activated, the magnet is accelerated upward, toward the solenoid center. When the solenoid is subsequently deactivated, gravity forces the magnet downward. This design reduces complexity compared to the two-solenoid oscillator, whereas the two-solenoid oscillator offers greater flexibility since the movement of the magnet in both directions is controlled.

The gravity-balanced oscillator (FIG. 4C) combines both simplicity and flexibility: Addition of a second magnet on top of the device makes it possible to trap the interior magnet at the top of the channel. As a result, the magnetic force of the single solenoid dominates oscillatory motion in both directions.

Figure 5:
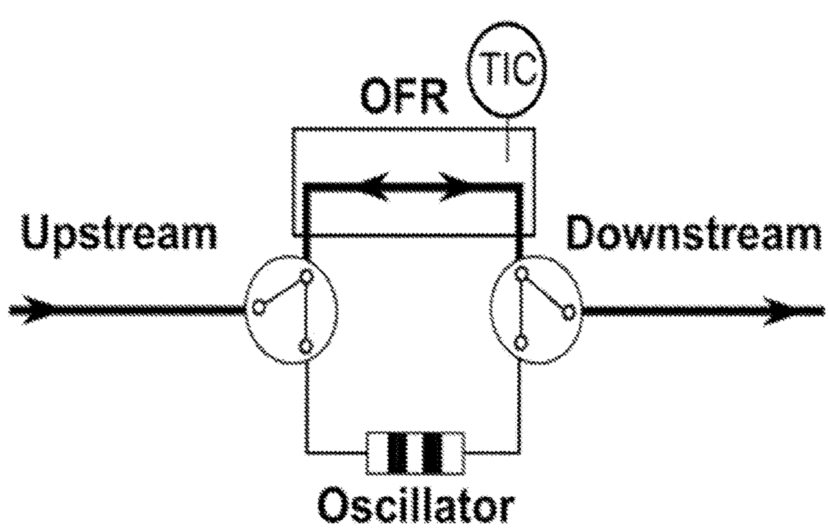
FIG. 5 is a schematic illustration of an oscillator as installed in an automated synthesis platform.

The integration of the device into the automated synthesis platform was achieved via an oscillatory flow cycle consisting of the device, a set of valves, and a custom-made oscillatory flow reactor as shown in FIG. 5. In FIG. 5, switching the positions of the valves allows one to decouple the oscillatory flow reactor from the main system. The cycle is symmetric and allows for stable, long-term oscillations at a variety of temperatures and pressures. The design is suitable for parallelization.

The oscillation cycle presented in FIG. 5 is entirely parallelizable. For example, multiple of these cycles can be integrated into an automated synthesis platform and operated in parallel at different temperatures and with different chemical composition of the reaction droplets. In some embodiments, parallel cycles can be run at different frequencies.

A set of specifications was developed to guide the design process of a new oscillation concept. These include:

Platform integration: It is desirable for the new reactor to be compatible with integration into an existing platform. It is also desirable to control the reactor via LabVIEW as is the remaining hardware for the sake of simplicity and reliability.

Displacement volume: According to the design of the platform, a displacement in the range of 0.01-0.1 mL was targeted. The ability to adjust the displacement volume within this range is considered desirable.

Lifetime: It is desirable for the oscillator to run with consistent performance for an extended period of time.

Chemical compatibility: It is desirable for the new design to be usable with a range of possible chemistries. If any material could possibly come into contact with substrates, it is desirable for that material to be inert. It is desirable for the materials to not exhibit limitations in terms of handling temperatures and pressures in the working range of the platform.

Oscillation Frequency: It is desirable for the new design to operate at a working frequency of at least 1 Hz. The capability to adjust the frequency between zero and a value of at least 1 Hz (and, in some cases, up to 100 Hz, up to 200 Hz, or more) is desirable.

Multiplexing: To render parallelized platforms more easily feasible, it is desirable for the oscillation mechanism itself to be parallelizable. From a financial perspective, this means that the costs per oscillation channel should be below the costs of the current setup that would require one syringe pump per channel when scaling out the existing oscillation mechanism.

A prototype was developed to satisfy the following requirements: ease of integration with existing liquid-handling hardware; access to a vast range of oscillation frequencies; compatibility with a wide array of chemical systems; and amenability to multiplexing. The prototype was also inexpensive and compact.

Solenoid Oscillator: Working Principles

Figure 6:
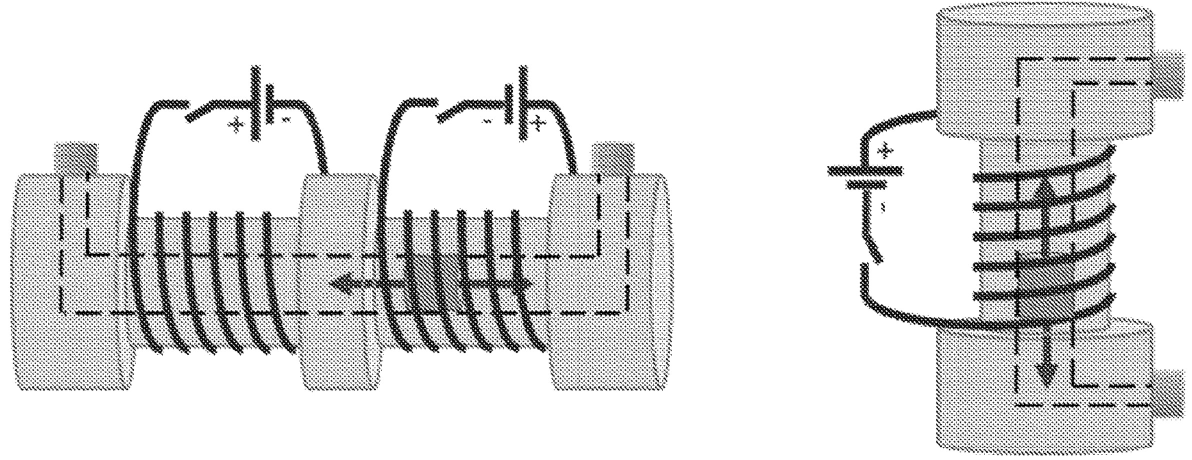
FIG. 6 shows schematic illustrations of a two-solenoid (left) and a single-solenoid (right) oscillator, according to certain embodiments.

FIG. 6 shows schematic illustrations of both a two-solenoid oscillator (TSO) and a single-solenoid oscillator (SSO) illustrating the final prototype designs. The magnet inside the two-solenoid prototypes oscillates between both solenoids. In the single-solenoid version, the magnet is attracted toward the center of the solenoid and is forced down by gravity. The solenoid circuits are closed and opened via either manual switches or automated relays.

The solenoid oscillator comprises a housing that encloses a magnetic piston and has two solenoids wrapped around the outside as shown in FIG. 6. By passing a current in one of the solenoids, the piston experiences a magnetic force and is attracted towards the solenoid. By alternatively switching the solenoids on and off, the piston is forced to oscillate inside the housing. When moving, the piston pushes and pulls the fluid inside the housing and thus creates an oscillatory flow that can be connected with the reactor.

This design allows one to satisfy all specifications mentioned above. Especially, the precise control of the solenoids via relay switches with switching times of around 20 ms allows full control over displacement volume and oscillation frequency. Chemical compatibility can be achieved using a variety of materials for the housing (e.g., PTFE and other materials). A range of magnets was tested to ensure both chemical compatibility and functionality, including nickel-coated rare earth neodymium and ceramic magnets.

Alternative designs involving one solenoid only were also investigated. Here, the oscillator was arranged vertically, leveraging gravity as force pushing down the magnet when the solenoid is turned off.

In addition to permanent magnets (e.g., rare-earth magnets, ceramic magnets), ferrofluids and magnetic ionic liquids were investigated as alternative to a permanent magnetic piston.

Figure 7:
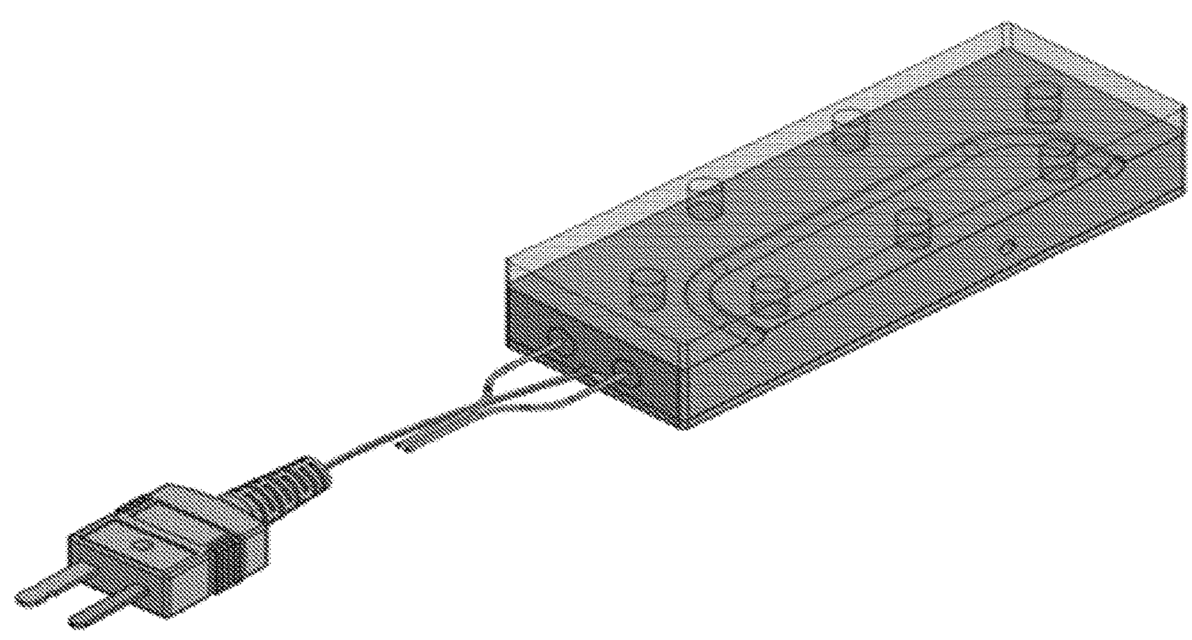
FIG. 7 is a schematic illustration of an oscillatory flow reactor, in accordance with some embodiments.

FIG. 7 is a schematic illustration of an oscillatory flow reactor that was integrated into a platform, in accordance with some embodiments. A FEP tube of 1/16" ID and 1/8" OD was squeezed between two layers of aluminum. The linear part of the tube inside the reactor was 2" long and was used to oscillate the droplet. Two cartridge heaters of length 3.25" with a power of 60 W and a thermocouple were integrated into the reactor.

To confirm the functionality of the prototypes, one setup was prepared that used manual mechanical switches to turn the solenoids on and off. This setup was shown to successfully induce oscillation in the magnet.

Figure 8:
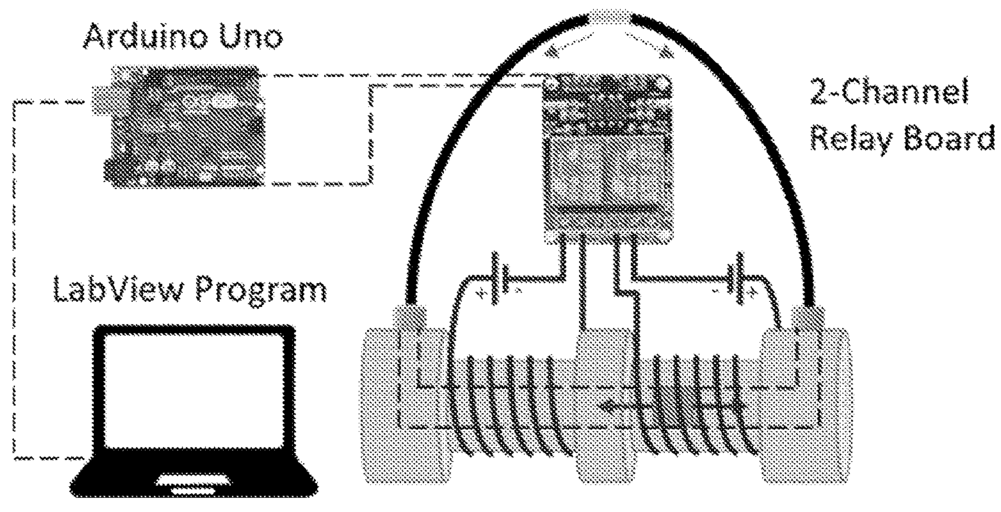
FIG. 8 is a schematic illustration of one example of an oscillatory flow system, according to certain embodiments.

The oscillation process was later automated via the incorporation of relay switches that were controlled via LabVIEW using an Arduino Uno R3 microcontroller. A schematic of one such system is shown in FIG. 8.

This setup was used to study the sensitivity of various parameters including:

Liquid vs. Gas as carrier phase

Piston type and size

Design: Two-solenoid vs. single-solenoid

Cycle time

Figure 9A:
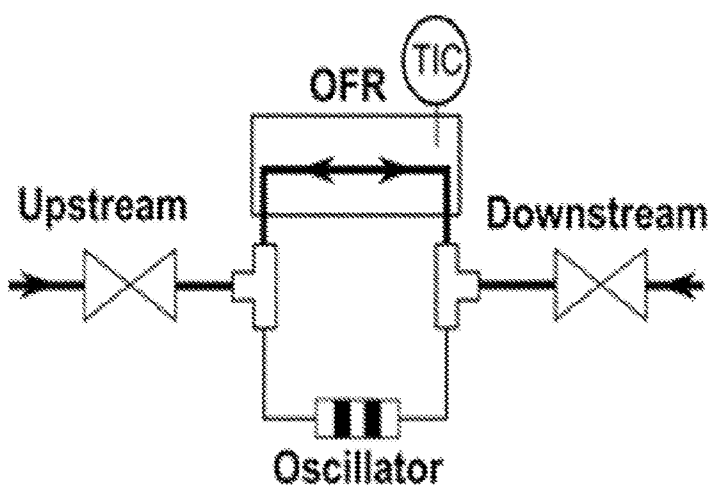
FIGS. 9A-9C are schematic illustrations of three oscillatory flow systems, in accordance with certain embodiments.

Several approaches to integrating the prototype with existing liquid handling equipment were evaluated:

2-way valve setup: See FIG. 9A. The valves are around the oscillation cycle, decoupling it from the main system while oscillating. To construct the 2-way valve setup, solenoid valves from Cole-Parmer (01540-03) were used with a working range up to 60 psi and 75° C.

Figure 9B:
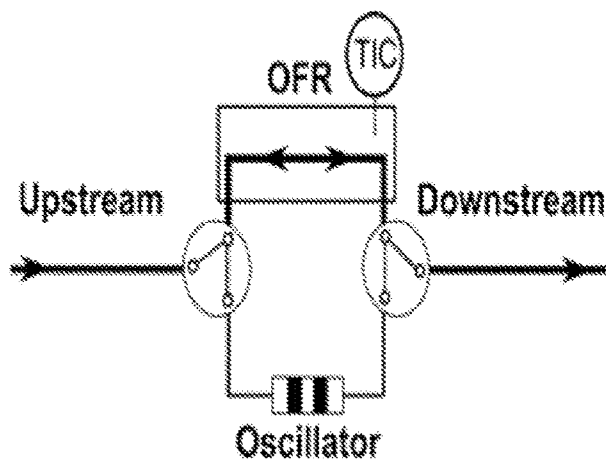

3-way valve setup: See FIG. 9B. A major benefit compared to the 2-way valves is that no additional T-junctions are required, thus simplifying the system. In consequence, the oscillator was fully decoupled from the main system when not running. This minimizes contamination by, e.g., rinse droplets that otherwise partially enter the tubes towards the oscillator. Neptune Research solenoid valves (HPAT031IC) were implemented into the 3-way valve setup with working range up to 75° C. and 100 psi. The interior of both valves is made of PTFE to ensure chemical compatibility.

Figure 9C:
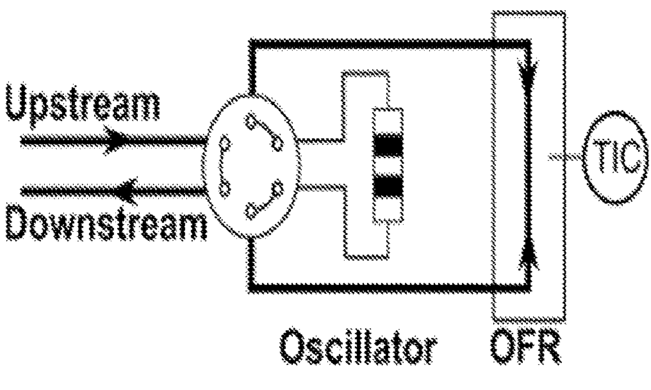

6-way valve setup: See FIG. 9C. The use of six-port, two-position valves such as those available from VICI Valco has been studied. These valves allow for oscillation at much higher pressures than the aforementioned setups.

Figure 10:
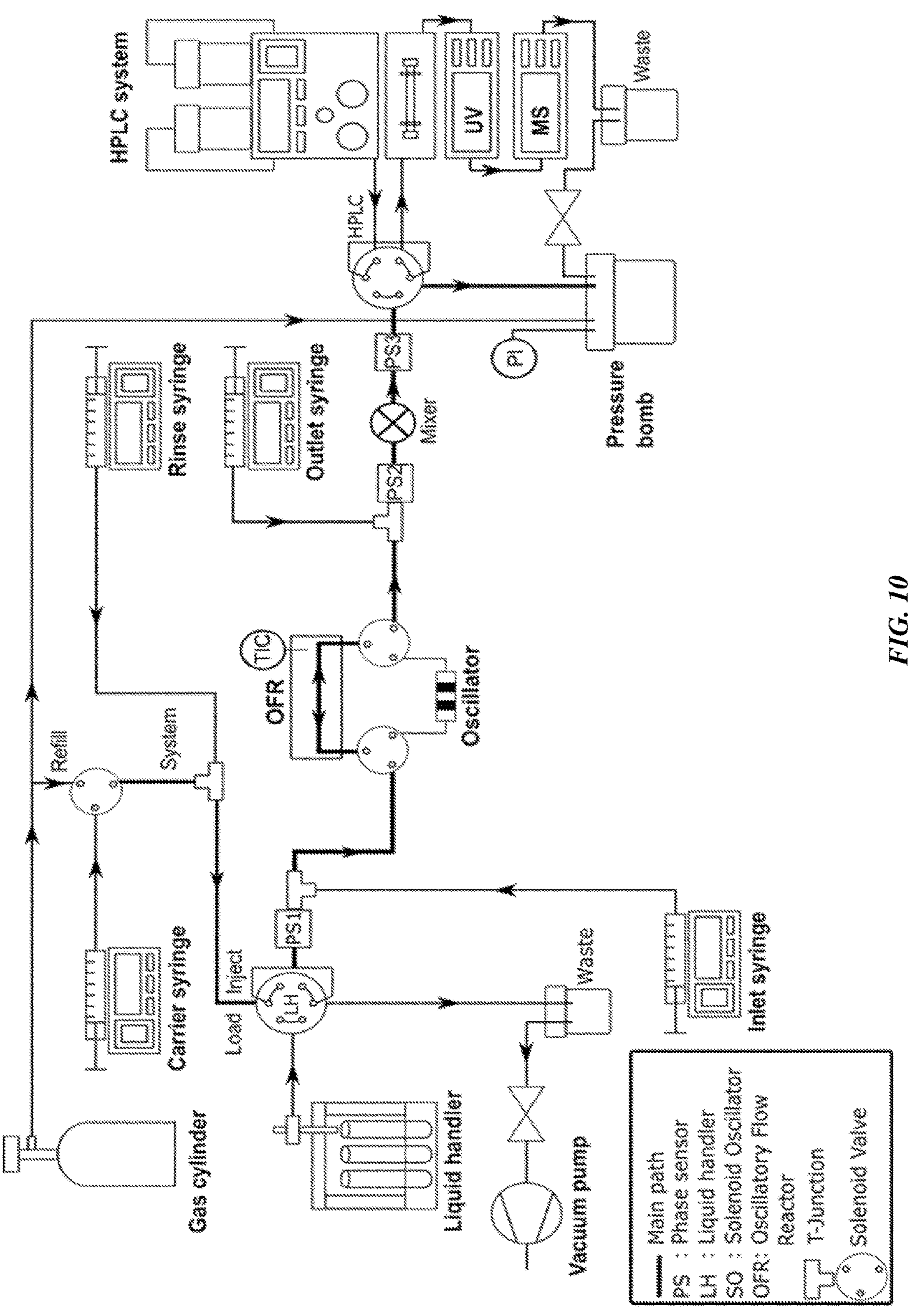
FIG. 10 is a schematic illustration of a flowchart of a platform setup that was used for certain oscillation studies, in accordance with certain embodiments.

FIG. 10 is a schematic illustration of a flowchart of the platform setup that was used for oscillation studies, in accordance with certain embodiments. (This figure is derived from Baumgartner et al., *Organic Process Research & Development* 2019, 23, 1594-1601.) The path of reaction droplets is marked in bold.

During operation, the oscillatory flow reactor (OFR) was oriented with its main channel arranged horizontally and with its inlet and outlet channels arranged vertically. (See, e.g., the schematic illustration of FIG. 5.) The OFR would hang from the inlet and outlet tubes (i.e., the inlet and outlet were in a vertical direction and the linear path inside the reactor was horizontal). This was done to leverage gravity effects to prevent the droplet from moving outside the reactor.

Besides the integration of the oscillation cycle, further hardware was added. A dual output DC power supply (Electro Industries Model 303D) was installed to provide DC power for both oscillator and solenoid valves. One output channel was used to power the solenoids of the oscillators and the second one for the solenoid valves. An Arduino Uno R3 microcontroller was used to control solenoids and valves via an 8-channel electromechanical relay board in LabView.

It was found that several parameters were helpful for achieving stable oscillations inside the platform:

Enhanced stability was achieved when the pressure level inside the oscillation cycle was similar to the up- and downstream parts of the platform to avoid initial flushing.

Enhanced performance was achieved when the position of the magnet inside the prototype was the same at the beginning of each oscillation run to increase reproducibility.

Enhanced performance was achieved when no liquid entered the oscillator, which avoided adverse impacts on oscillation performance.

To conduct oscillation studies close to real experimental conditions inside the platform, said studies were carried out at an elevated pressure of 70 psi and the droplet volume was the same as used for reaction droplets in the platform, i.e., 17 μL. The following studies were carried out:

Long-term stability: Overnight runs

Effects of piston type and size

Effects of hydrodynamic resistance

Figure 11:
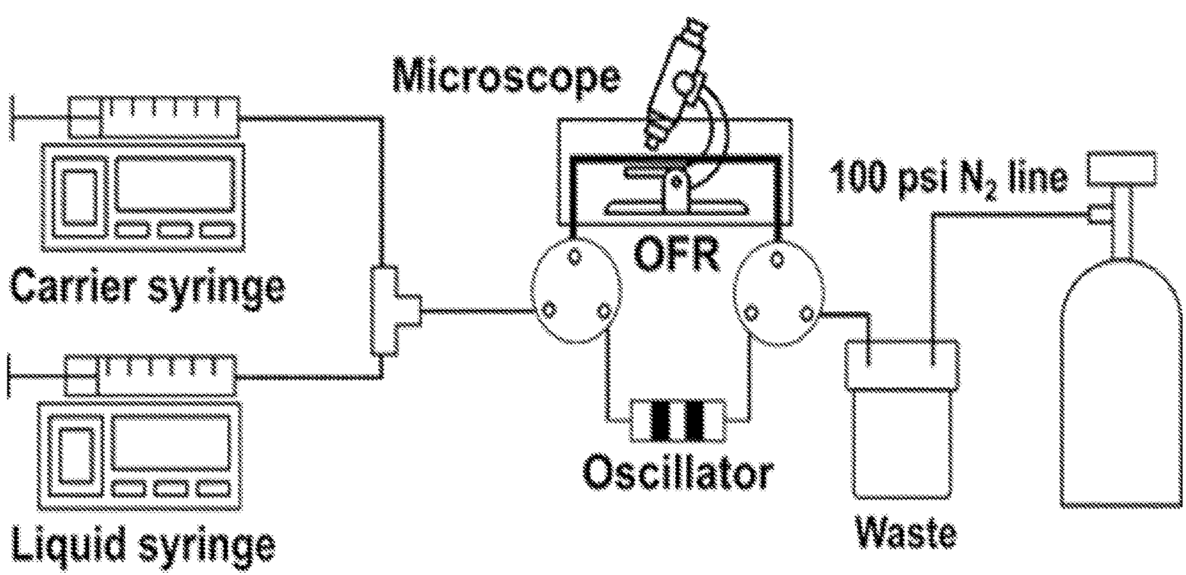
FIG. 11 is a schematic illustration of an experimental setup that was used for certain oscillation studies, in accordance with certain embodiments.

Motivated by differences in results from proof-of-concept and platform studies, an additional setup was developed aiming to study the oscillation outside the platform at conditions similar to those inside the platform. This was achieved by using the same set of valves, a similar linear aluminum reactor and similar tube lengths—basically creating a copy of the oscillation cycle in the platform. Also, it was designed to be able to handle pressures up to 100 psi. A stereomicroscope (Leica MZ 12, light source Fiber-Lite PL-800) with integrated camera (Canon PC 1234) was used for the visualization of oscillation properties as shown in FIG. 11. A microscope with integrated digital camera was used to take photos and videos of the oscillation. All syringe pumps, valves and solenoids were controlled via LabView. The nitrogen line allowed for pressures of up to 100 psi.

This setup was used to study the following parameters:

Pressure: Study at 15 psi, 50 psi and 80 psi

Piston type and size

Hydrodynamic resistance

To evaluate the mixing capabilities of the system, the performance of a series of reactions known to be mixing-sensitive (either due to the multiphasic nature of the reactions, or to the kinetics of competing reactions) were studied in the system. The reaction systems that were studied include a set of parallel competitive reactions in which acid-catalyzed hydrolysis of dimethoxypropane competes with acid-base neutralization (See Organic Process Research & Development 2003, 7, 471-508 and scheme below) and a biphasic Suzuki coupling reaction (See Chemical communications 2017, 53, 6649-6652.):

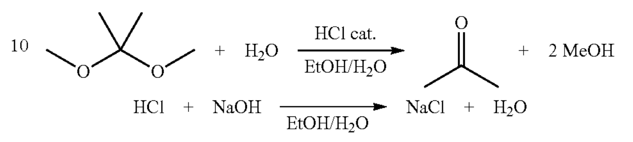

The underlying concept behind the set of parallel competitive reactions is that the yield of acetone depends on mixing. Acid is added to a basic solution of DMP; the total amount of base in the system is to be larger than the added acid. In an ideally mixed system, all acid would be neutralized faster than the characteristic time of DMP hydrolysis and consequently, very little acetone would be generated. In case of purely diffusive mixing, pH depends on position and hydrolysis takes place in some parts of the reactor. A larger yield would be the consequence.

Figure 12:
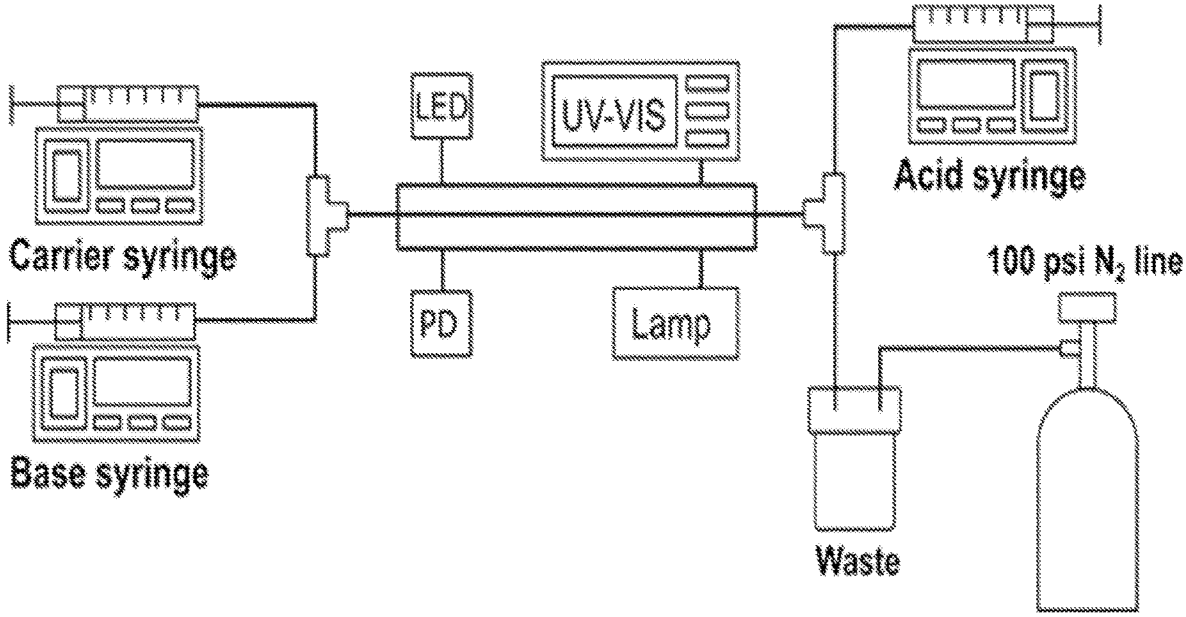
FIG. 12 is a schematic illustration of an experimental setup for mixing studies, in accordance with some embodiments.

An experimental setup was designed to run the Bourne reactions in oscillatory flow as illustrated in FIG. 12. The setup (including three syringe pumps, the photodetector and the UV-Vis spectrometer) was automated and controlled via LabView to increase reproducibility. The nitrogen line allows for pressures of up to 100 psi.

A basic solution of 400 mM DMP in 350 mM KOH and an acidic solution of 250 mM HCl, both in 30 wt. % ETOH in water, were prepared and filled in the syringe pumps. Harvard Apparatus PHD Ultra pumps were used and equipped with 20 mL BD Luer-Lok syringes. After pressurization to 50 psi, three 15 μL rinse droplets of base were introduced to the system and after these passed the acid syringe, three 15 μL acid rinse droplet were introduced. When all rinse droplets reached the waste bottle, a 50 μL base droplet was injected and moved towards the acid syringe, where 50 μL acid was added to the droplet. The droplet was then moved inside the reactor between the optical detection pairs; whenever reaching a detector, the direction of flow was inverted to let the droplet oscillate. The yield of acetone was tracked using UV-Vis spectroscopy with an Ocean Optics HR 2000+ spectrometer and a DH-2000-BAL deuterium and halogen lamp. For every cycle, a UV-Vis spectrum was measured to monitor the change in droplet composition during the reaction, with an integration time of 20 ms and averaged over 10 spectra. To generate a calibration curve, solutions corresponding to different reaction outcomes were prepared and spectra were measured.

For both reaction types, the measured conversion confirmed that the oscillator prototype delivers effective mixing.

Figure 13:
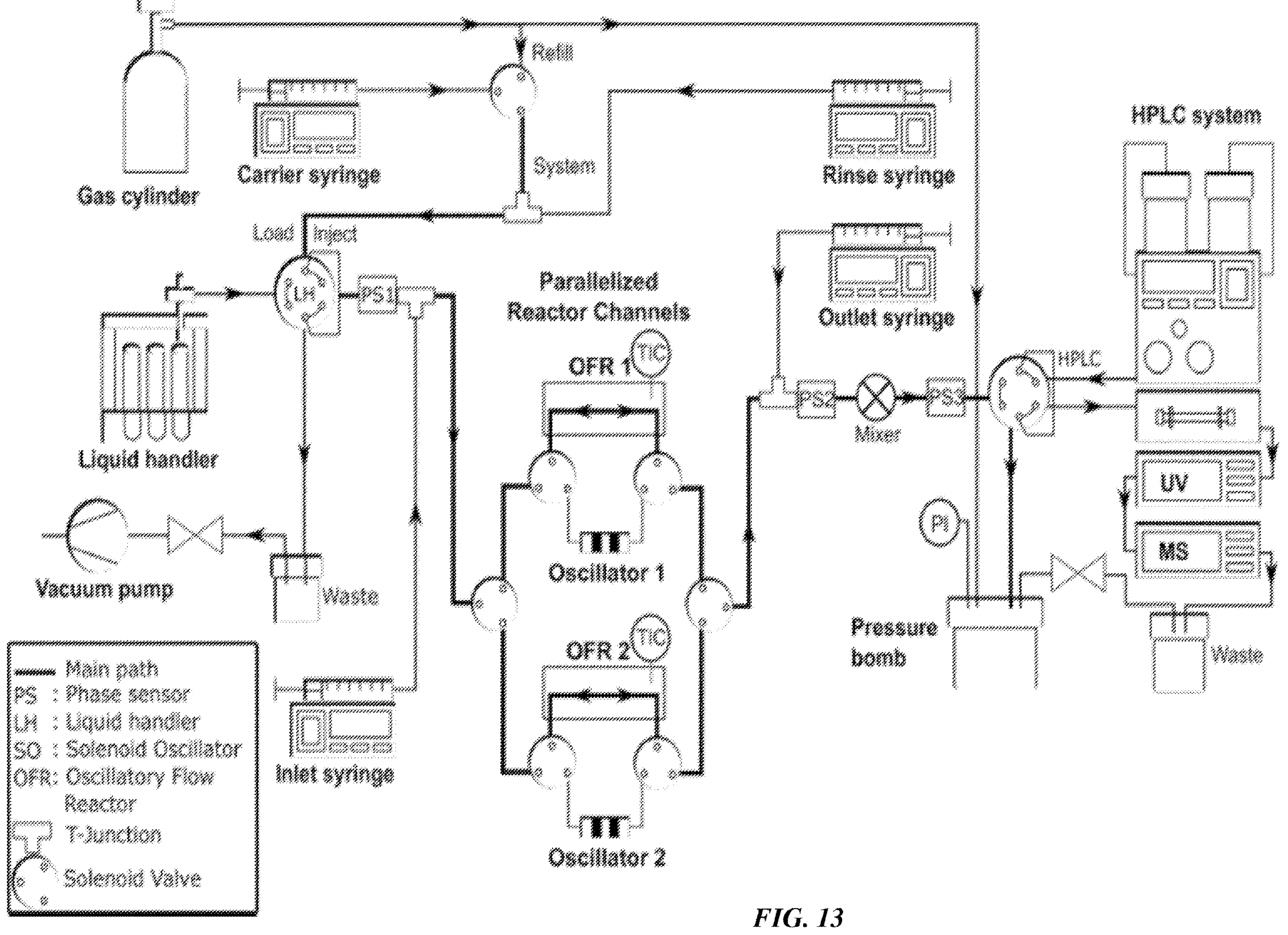
FIG. 13 is a schematic illustration of a two-channel platform, in accordance with certain embodiments.

Multiplexing is a central concept in high throughput experimentation platforms. When running only one reaction at a time, throughput is consequently limited. One objective of this work, therefore, comprised the integration of parallel reactors into the platform. As a first step toward multiplexing, the current automated platform was equipped with a second channel and its software updated to be capable of handling two reactions at the same time. In doing so, the software was rewritten in a way that allowed further extensions to control platforms with more channels. Major modifications had to be done to allow the platform to handle parallel channels. The integration of the additional hardware is illustrated in FIG. 13 (derived from Baumgartner et al., *Organic Process Research & Development* 2019, 23, 1594-1601). Two solenoid valves act as selector valves for the channels. This setup can easily be expanded to larger numbers of channels (e.g., 4, 8, 16, or more channels) by, for example, the incorporation of multi-channel selector valves.

The operational parameters are the only ones that can be influenced during a running oscillation experiment. The oscillation studies generally were conducted in a voltage working range of 1-30 V (although solenoids compatible with higher voltages could also be incorporated) and 0-1 s active time $\tau$ (although longer active times are feasible). To avoid heating issues during runs with both high V and $\tau$, all experiments were carried out with active air-cooling. Low-resistance commercial solenoids (such as those available from APW Electromagnets) have also been tested, and have been found not to require air cooling.

Based on the determined dependency of displacement on hydrodynamic resistance and pressure, the impact of the working fluid itself was investigated with focus on liquid versus gas filling of the oscillator. To carry out runs with liquid-filled devices in a reproducible way, the entire system was set under liquid and a gas bubble was tracked for displacement determination.

Neither overshoots nor droplet breakups were observed for any liquid-based experiments, rendering the oscillator suitable for liquid-based microfluidic setups.

This is assumed to be a result of both the liquid's incompressibility and higher density compared to gaseous systems. The magnet experiences a larger drag force and consequently, its maximum velocity is reduced. It appears to be likely that liquid oscillation does not depend on pressure, again due to the liquid's incompressibility.

The single-solenoid oscillator is an alternative, simplified design of the two-solenoid oscillator leveraging gravity to push back the magnet in its initial position. Due to its different functionality, its oscillation behavior was found to differ from the two-solenoid design. The concept is illustrated in FIG. 4C. In FIG. 4C, a magnet is integrated into the top part of the device to overcome gravity. In the left-hand side of FIG. 4C, the magnet is pushed upward when the solenoid is activated and the magnet remains at the top due to the attraction force towards the second magnet. In the right-hand side of FIG. 4C, the magnet is pushed downward when the solenoid is activated again.

Generally, this experiment proves the functionality of the single-solenoid design. Further tests were done inside the automated platform to identify suitable parameters for a stable oscillation. Due to the limited degrees of freedom compared to the two-solenoid design (neither magnet size nor gravity could be influenced), the design provides less flexibility to tune the oscillation according to the specific needs of a setup.

The oscillator prototype has been found to be easily multiplexable. One way to achieve this is to connect several of oscillator loops to a multi-port selector valve. Using this setup, it was found that the separate loops did not interfere with one another.

In addition, oscillation of biphasic droplets inside the automated droplet platform were successfully carried out and shown to be stable for 1 hr.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The above-described embodiments can be implemented in any of numerous ways. For example, embodiments of designing and making the technology disclosed herein may be implemented using hardware, software or a combination thereof. When implemented in software, the software code can be executed on any suitable processor or collection of processors, whether provided in a single computer or distributed among multiple computers. Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device. Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format. Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may, in some embodiments, be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments. Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A device, comprising:

a first fluidic channel;

a second fluidic channel;

a fluidic loop between and fluidically connected to the first fluidic channel and the second fluidic channel;

valving configured such that:

when the valving is in a first position, the valving establishes fluid communication between the first fluidic channel and a first connection of the fluidic loop, and the valving establishes fluid communication between the second fluidic channel and a third connection of the fluidic loop, and when the valving is in a second position, the valving establishes fluid communication between the first connection of the fluidic loop and a second connection of the fluidic loop, and the valving establishes fluid communication between the third connection of the fluidic loop and a fourth connection of the fluidic loop;

a magnetically-susceptible body within the fluidic loop; and at least one solenoid associated with the fluidic loop and configured such that, upon application of a voltage to the at least one solenoid, the at least one solenoid generates a magnetic field that causes movement of the magnetically-susceptible body along the fluidic loop, wherein the at least one solenoid is configured such that oscillatory flow of the magnetically-susceptible body is produced by applying a voltage to the at least one solenoid to transport the magnetically-susceptible body against the force of gravity and removing the applied voltage to allow the magnetically-susceptible body to move with the force of gravity.

2. The device of claim 1, wherein the at least one solenoid surrounds at least a portion of the fluidic loop.

3. The device of claim 1, wherein the fluidic loop comprises a reactor.

4. The device of claim 1, wherein the magnetically-susceptible body is a solid body.

5. The device of claim 1, wherein the magnetically-susceptible body comprises a magnetically-susceptible fluid.

6. The device of claim 5, wherein the magnetically-susceptible fluid is a ferrofluid.

7. A device, comprising:

a first fluidic channel;

a second fluidic channel;

a fluidic loop between and fluidically connected to the first fluidic channel and the second fluidic channel;

valving configured such that:

when the valving is in a first position, the valving establishes fluid communication between the first fluidic channel and a first connection of the fluidic loop, and the valving establishes fluid communication between the second fluidic channel and a third connection of the fluidic loop, and when the valving is in a second position, the valving establishes fluid communication between the first connection of the fluidic loop and a second connection of the fluidic loop, and the valving establishes fluid communication between the third connection of the fluidic loop and a fourth connection of the fluidic loop;

a magnetically-susceptible body within the fluidic loop; and at least one solenoid associated with the fluidic loop and configured such that, upon application of a voltage to the at least one solenoid, the at least one solenoid generates a magnetic field that causes movement of the magnetically-susceptible body along the fluidic loop, wherein the valving comprises a single valve.

8. The device of claim 7, wherein the single valve is a single six-way valve.

9. The device of claim 7, wherein the device comprises a first solenoid and a second solenoid configured such that oscillatory flow of the magnetically-susceptible body is produced by applying alternating voltages between the first solenoid and the second solenoid.

10. The device of claim 7, wherein the fluidic loop comprises a reactor.

11. The device of claim 7, wherein the magnetically-susceptible body is a solid body.

12. The device of claim 7, wherein the magnetically-susceptible body comprises a magnetically-susceptible fluid.

13. A device, comprising:

a first fluidic channel;

a second fluidic channel;

a fluidic loop between and fluidically connected to the first fluidic channel and the second fluidic channel;

valving configured such that:

when the valving is in a first position, the valving establishes fluid communication between the first fluidic channel and a first connection of the fluidic loop, and the valving establishes fluid communication between the second fluidic channel and a third connection of the fluidic loop, and when the valving is in a second position, the valving establishes fluid communication between the first connection of the fluidic loop and a second connection of the fluidic loop, and the valving establishes fluid communication between the third connection of the fluidic loop and a fourth connection of the fluidic loop;

a magnetically-susceptible body within the fluidic loop; and at least one solenoid associated with the fluidic loop and configured such that, upon application of a voltage to the at least one solenoid, the at least one solenoid generates a magnetic field that causes movement of the magnetically-susceptible body along the fluidic loop, wherein the valving comprises at least two 3-way valves.

14. The device of claim 13, wherein the fluidic loop comprises a reactor.

15. The device of claim 13, wherein the magnetically-susceptible body is a solid body.

16. The device of claim 13, wherein the magnetically-susceptible body comprises a magnetically-susceptible fluid.

17. A device, comprising:

a first fluidic channel;

a second fluidic channel;

a fluidic loop between and fluidically connected to the first fluidic channel and the second fluidic channel;

valving configured such that:

when the valving is in a first position, the valving establishes fluid communication between the first fluidic channel and a first connection of the fluidic loop, and the valving establishes fluid communication between the second fluidic channel and a third connection of the fluidic loop, and when the valving is in a second position, the valving establishes fluid communication between the first connection of the fluidic loop and a second connection of the fluidic loop, and the valving establishes fluid communication between the third connection of the fluidic loop and a fourth connection of the fluidic loop;

a magnetically-susceptible body within the fluidic loop; and at least one solenoid associated with the fluidic loop and configured such that, upon application of a voltage to the at least one solenoid, the at least one solenoid generates a magnetic field that causes movement of the magnetically-susceptible body along the fluidic loop, wherein the device further comprises a magnet adjacent to the fluidic loop, the magnet and the at least one solenoid configured such that oscillatory flow of the magnetically-susceptible body is produced by applying a first voltage to the at least one solenoid to transport the magnetically-susceptible body against the force of gravity and toward the magnet, and applying a second voltage to the at least one solenoid to transport the magnetically-susceptible body with the force of gravity and away from the magnet.

18. The device of claim 17, wherein the fluidic loop comprises a reactor.

19. The device of claim 17, wherein the magnetically-susceptible body is a solid body.

20. The device of claim 17, wherein the magnetically-susceptible body comprises a magnetically-susceptible fluid.

* * * * *